(12) United States Patent
Diao et al.

(10) Patent No.: US 9,254,122 B2
(45) Date of Patent: Feb. 9, 2016

(54) REUSABLE HANDPIECE FOR DISPOSABLE PROBES

(75) Inventors: Edward Diao, San Francisco, CA (US); Rajan Kashibhai Patel, Woodside, CA (US)

(73) Assignee: Socorro Medical, Inc., San Francisco, CA (US)

( * ) Notice: Subject to any disclaimer, the term of this patent is extended or adjusted under 35 U.S.C. 154(b) by 752 days.

(21) Appl. No.: 12/630,172

(22) Filed: Dec. 3, 2009

(65) Prior Publication Data

US 2010/0206099 A1 Aug. 19, 2010

Related U.S. Application Data

(60) Provisional application No. 61/119,682, filed on Dec. 3, 2008.

(51) Int. Cl.
| | |
|---|---|
| G01D 21/00 | (2006.01) |
| A61B 10/06 | (2006.01) |
| A61B 17/29 | (2006.01) |
| A61B 17/295 | (2006.01) |
| A61B 17/32 | (2006.01) |
| A61B 17/16 | (2006.01) |

(Continued)

(52) U.S. Cl.
CPC ............ *A61B 10/06* (2013.01); *A61B 17/295* (2013.01); *A61B 17/2909* (2013.01); *A61B 17/320036* (2013.01); *A61B 17/1608* (2013.01); *A61B 17/1611* (2013.01); *A61B 17/1686* (2013.01); *A61B 2017/00464* (2013.01); *A61B 2017/2946* (2013.01); *A61B 2019/4842* (2013.01); *A61B 2019/4857* (2013.01)

(58) Field of Classification Search
CPC ...... A61B 17/32; A61B 17/295; A61B 10/06; A61B 17/320036; A61B 17/29; A61B 2017/2946; A61B 2017/2842; A61B 2017/2857; A61B 17/2909; A61B 17/1608; A61B 17/1611; A61B 17/1686; A61B 2017/00464
See application file for complete search history.

(56) References Cited

U.S. PATENT DOCUMENTS

| | | | | |
|---|---|---|---|---|
| 5,029,573 A | * | 7/1991 | Chow | 600/104 |
| 5,318,582 A | * | 6/1994 | Chow | 606/170 |
| 5,667,473 A | * | 9/1997 | Finn et al. | 600/104 |

(Continued)

FOREIGN PATENT DOCUMENTS

| | | |
|---|---|---|
| JP | 10-005236 | 1/1998 |
| JP | 2008098253 | 8/2008 |

(Continued)

OTHER PUBLICATIONS

International Search Report and Written Opinion, PCT/US2009/066532, dated Jul. 14, 2010, 12 pages.

(Continued)

*Primary Examiner* — Gary Jackson
*Assistant Examiner* — Scott T Luan
(74) *Attorney, Agent, or Firm* — Dorsey & Whitney LLP

(57) ABSTRACT

A handpiece for removably attaching one of a plurality of probes including a housing, an actuation assembly arranged on the housing, a linkage assembly arranged on the housing and adapted to couple motion of the actuation assembly to actuation of the probe and an alignment feature arranged on the housing and adapted to control the orientation of a connected probe. Several probes are also disclosed in addition to method of performing a procedure.

22 Claims, 50 Drawing Sheets

(51) Int. Cl.
*A61B 17/00* (2006.01)
*A61B 19/00* (2006.01)

(56) References Cited

U.S. PATENT DOCUMENTS

| | | | |
|---|---|---|---|
| 5,827,323 A | 10/1998 | Klieman et al. | |
| 5,888,200 A | 3/1999 | Walen | |
| 6,024,744 A * | 2/2000 | Kese et al. | 606/51 |
| 6,206,877 B1 * | 3/2001 | Kese et al. | 606/48 |
| 6,527,786 B1 * | 3/2003 | Davis et al. | 606/151 |
| 2001/0014806 A1 | 8/2001 | Ellman et al. | |
| 2003/0055424 A1 | 3/2003 | Ciarrocca | |
| 2004/0230133 A1 | 11/2004 | Miller et al. | |
| 2006/0025793 A1 | 2/2006 | Gibson et al. | |
| 2008/0118709 A1 | 5/2008 | Sims et al. | |
| 2009/0221876 A1 * | 9/2009 | Cobb et al. | 600/201 |
| 2010/0057078 A1 * | 3/2010 | Arts et al. | 606/41 |
| 2012/0022538 A1 * | 1/2012 | Schmitz et al. | 606/79 |

FOREIGN PATENT DOCUMENTS

| | | |
|---|---|---|
| WO | WO01/60261 | 8/2001 |
| WO | WO2006/104836 | 10/2006 |
| WO | WO2007/121109 | 10/2007 |
| WO | WO2008/098253 | 8/2008 |
| WO | WO2008/118709 | 10/2008 |

OTHER PUBLICATIONS

First Office Action dated Nov. 21, 2012, CA Patent Application No. 2,745,802, 2 pages.
First Office Action dated Apr. 28, 2013, CN Patent Application No. 200980155899.1, 17 pages.
First Office Action dated Sep. 4, 2012, AU Patent Application No. 2009322332, 4 pages.
Notice of Reasons for Rejection, Japanese Patent Application No. 2011-539684, dated Sep. 3, 2013, 5 Pages.

* cited by examiner

PREPARATION OF SURGICAL SITE
- place an incision in the wrist of a patient
- place a small transverse incision through the antibrachial fascia to expose the bursa
- open antibrachial fascia longitudinally and distally
- elevate the synovium and locate the underside of the transverse carpal ligament
- continue elevating synovium from the transverse carpal ligament

~802

PREPARE DEVICE
- align alignment feature of first probe with an alignment feature on handpiece
- secure retaining cap over probe base assembly to attach first probe to handpiece

~804

PERFORM FIRST PORTION OF PROCEDURE
- insert a first probe within the carpal tunnel
- use endoscope to visualize target structures and non-target structures
- adjust position of probe in response to relative location of structures
- slide cannula proximally as required to expose a probe tool on the first probe
- perform first portion of procedure with first probe
- slide cannula distally to maintain the surgical site
- remove first probe

~806

EXCHANGE PROBES
- remove retaining cap from handpiece to free first probe
- remove first probe from the handpiece
- align alignment feature of second probe with an alignment feature on handpiece
- secure retaining cap over probe base assembly to attach second probe to handpiece

~808

PERFORM SECOND PORTION OF PROCEDURE
- inserting the second probe into the surgical site by placing it within the place holding cannula
- use endoscope to visualize structures and verify proper placement of probe
- adjust probe position in response to structure locations
- move place holding cannula proximally to expose probe tool
- release locking mechanism
- actuate actuation mechanism to deploy probe tool
- translate handpiece distally and/or proximally to sever the ligament

~810

ADDITIONAL INTERCHANGES
- repeat probe exchange steps and perform additional portions of procedure as required

REUSABLE HANDPIECE FOR DISPOSABLE PROBES

CROSS-REFERENCE TO RELATED APPLICATIONS

The present application claims priority to U.S. Provisional Patent Application No. 61/119,682 filed on Dec. 3, 2008, entitled Reusable Handpiece for Disposable Probes and Exemplary Probe Having Stationary Scoop Retractor with Bidirectional Mobile Blade for Neural Decompression, the contents of which are hereby incorporated by reference herein in their entirety.

FIELD OF THE INVENTION

The following description relates to a medical apparatus and surgical methods. More specifically, the description relates to an instrument and to methods for minimally invasive surgical procedures in constrained spaces of the body. Even more particularly the description relates to a handpiece, interchangeable with several probes, where the handpiece can be used to manipulate the probes to perform carpal tunnel release or ulnar nerve decompression procedures or other related procedures.

BACKGROUND OF THE INVENTION

Minimally invasive surgeries are well known and often involve an endoscopic or arthroscopic procedure where incisions are minimized and the surgery is performed within the body using one or more portals for insertion of instruments together with a camera or scope for viewing and conducting the procedure. Having contacted human fluids during use, the devices used for performing these procedures require that they either be sterilized or disposed of.

The choice between sterilization and disposal can often be balanced between the cost of the tool or device and the difficulty in sterilizing the device. Where the cost to replace it is low and/or the difficulty in sterilizing is high, the device will likely be discarded and replaced. In some instances, this may include discarding portions of the device that did not actually contact the patient. That is, where a portion of a device was inserted and another portion was not, the entire device likely is still discarded.

Minimally invasive surgeries often require multiple tools, wherein each tool is configured to perform a different function. Multiple tools increase sterilization and replacement costs.

There is a need for a minimally invasive medical tool configured to reduce sterilization and replacement costs. There is also a need in the art for methods of manufacturing and using such a medical tool.

SUMMARY

In one embodiment, a handpiece for removably attaching one of a plurality of probes can include a housing, an actuation assembly arranged on the housing, a linkage assembly arranged on the housing and adapted to couple motion of the actuation assembly to actuation of the probe, and an alignment feature arranged on the housing and adapted to control the orientation of a connected probe. The actuation assembly can include a pivotal member mounted on the housing with a pivot pin. The actuation assembly can further include a locking mechanism adapted to selectively lock the pivotal member in one of a plurality of positions. The locking mechanism can include a biased button telescopically mounted in the pivotal member via a locking pin. The button can include a locking pin and the housing can include a rack adapted to receive the locking pin thereby preventing pivoting of the pivotal member without depressing the button. Motion of the actuation assembly can be pivotal motion and the linkage assembly can be adapted for translational motion.

The linkage assembly of the above embodiment can include a translatable linkage member pivotally pinned to the pivotal member and adapted to isolate the longitudinal motion of the pivotal member. The pivotal member can include a slotted hole and the linkage member can be arranged on the housing via a longitudinal guide track, the slotted hole decoupling the vertical component of the pivotal motion of the pivotal member from the horizontal motion.

The alignment feature of the above embodiment can be associated with a distal end of the housing and can be adapted to control the radial orientation about the longitudinal axis of the housing of an attached probe. The alignment feature can include an annular recess positioned on a distal face of the housing and the alignment feature can include an asymmetrical orientation about the longitudinal axis of the housing thereby providing for a single orientation of an attached probe.

The handpiece can also include a retaining cap adapted to secure a probe to the handpiece. The retaining cap can be adapted to secure a portion of the probe against the alignment feature.

In another embodiment, a minimally invasive surgical assembly can include the handpiece described and a probe adapted for removable attachment to the handpiece. The probe can include a base assembly and a procedure assembly. The base assembly can include a stand off member adapted to engage the alignment feature.

In another embodiment, a probe for removable attachment to a handpiece can include a base assembly, a procedure assembly extending from the base assembly, the procedure assembly comprising an insertion member and a probe tool positioned on the insertion member for selective deployment. The insertion member can include a cavity at a distal end, the probe tool being positioned within the cavity. The procedure assembly can include a window adapted for viewing of anatomical structures on a side of the insertion tool opposite the probe tool.

The probe tool of the above embodiment can include a blade with a first cutting edge and can include a second cutting edge. The blade can also include a non-cutting edge disposed between the first and second edges or at a distal tip thereof, the non-cutting edge adapted to smoothly engage and separate target tissues from non-target tissues. The first cutting edge can be an arcuate distal edge and the second cutting edge can be a relatively straight proximal edge. The non-cutting edge can be a duckbill portion.

In another embodiment, a method of performing a procedure with interchangeable probes and a handpiece can include attaching a first probe to a handpiece, the probe having a place holding cannula positioned thereon, inserting the probe into a surgical site, performing a first portion of the procedure with the first probe, advancing the place holding cannula over the distal end of the first probe to maintain the surgical site, removing the first probe from the surgical site leaving the place holding cannula behind, removing and replacing the first probe with a second probe, inserting the second probe into the surgical site by placing the second probe with the place holding cannula, performing a second portion of the procedure with the second probe. Attaching the first probe and the second probe to the handpiece can include aligning the alignment features of the probe with corresponding alignment features of the handpiece. Attaching the first probe and the second probe to the handpiece can also include securing the respective probe with a retaining cap.

In the above embodiment, performing either the first portion of the procedure or the second portion of the procedure can include obtaining a pressure measurement at the surgical site. Performing a portion of the procedure can also include deploying a probe tool on the probe. Additionally, performing a procedure can include releasing a locking mechanism and actuating an actuation mechanism. Releasing a locking mechanism can include depressing a button thereby freeing the actuation mechanism to move and actuating an actuation mechanism can include pivoting a pivotal member. Deploying a probe tool can also include reengaging a locking mechanism where reengaging the locking mechanism can include releasing a depressed button.

The method described can also include repeating a portion of the method. Particularly this may include removing and replacing the probe, inserting the replacement probe, and performing an additional portion of the procedure with the replacement probe While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIG. 47 is a chart of steps available for a method of performing a procedure.

DETAILED DESCRIPTION

The present disclosure relates to a handpiece for removably connecting a plurality of probes. The probes can be adapted for performing a wide range of procedures and can be interchanged with one another and/or disposed of without a need to dispose of the handpiece. The handpiece embodiments described can be used for performing a wide range of procedures including, but not limited to carpal tunnel release and cubital tunnel release procedures.

Figure 1:
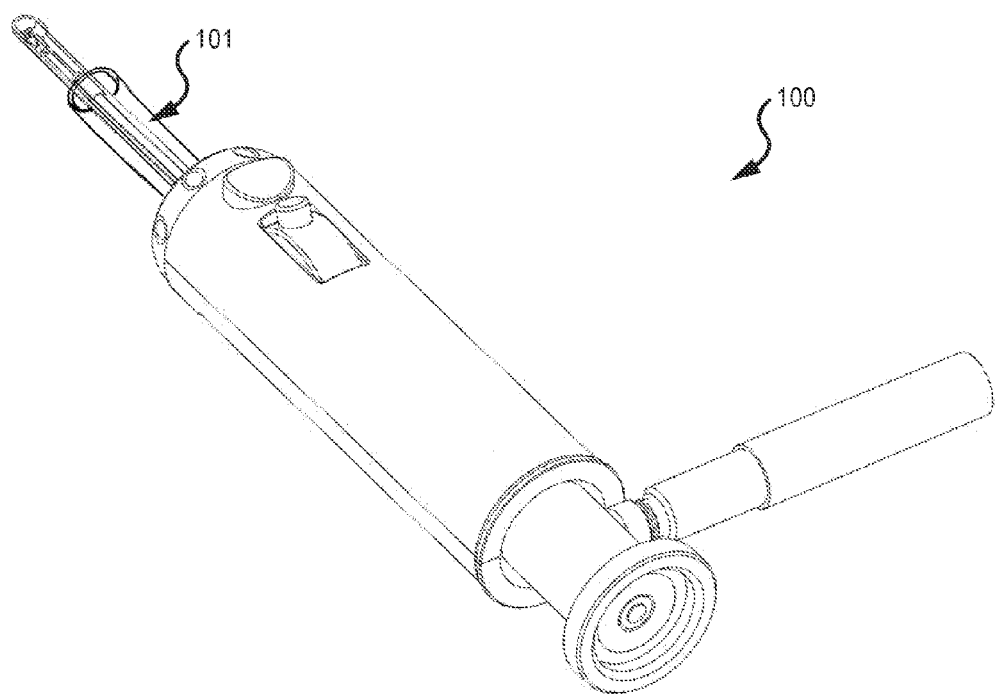
FIG. 1 is a perspective view of a handpiece according to one embodiment.

Referring now to FIG. 1, a handpiece 100 for use with disposable probes is shown. In some embodiment the handpiece 100 is a probe holder. In other embodiments the handpiece 100 may be a probe manipulation device. In the embodiment shown, the handpiece 100 is adapted to fit comfortably into the hand of a surgeon and is further adapted to both hold a probe and manipulate the probe.

Figure 2:
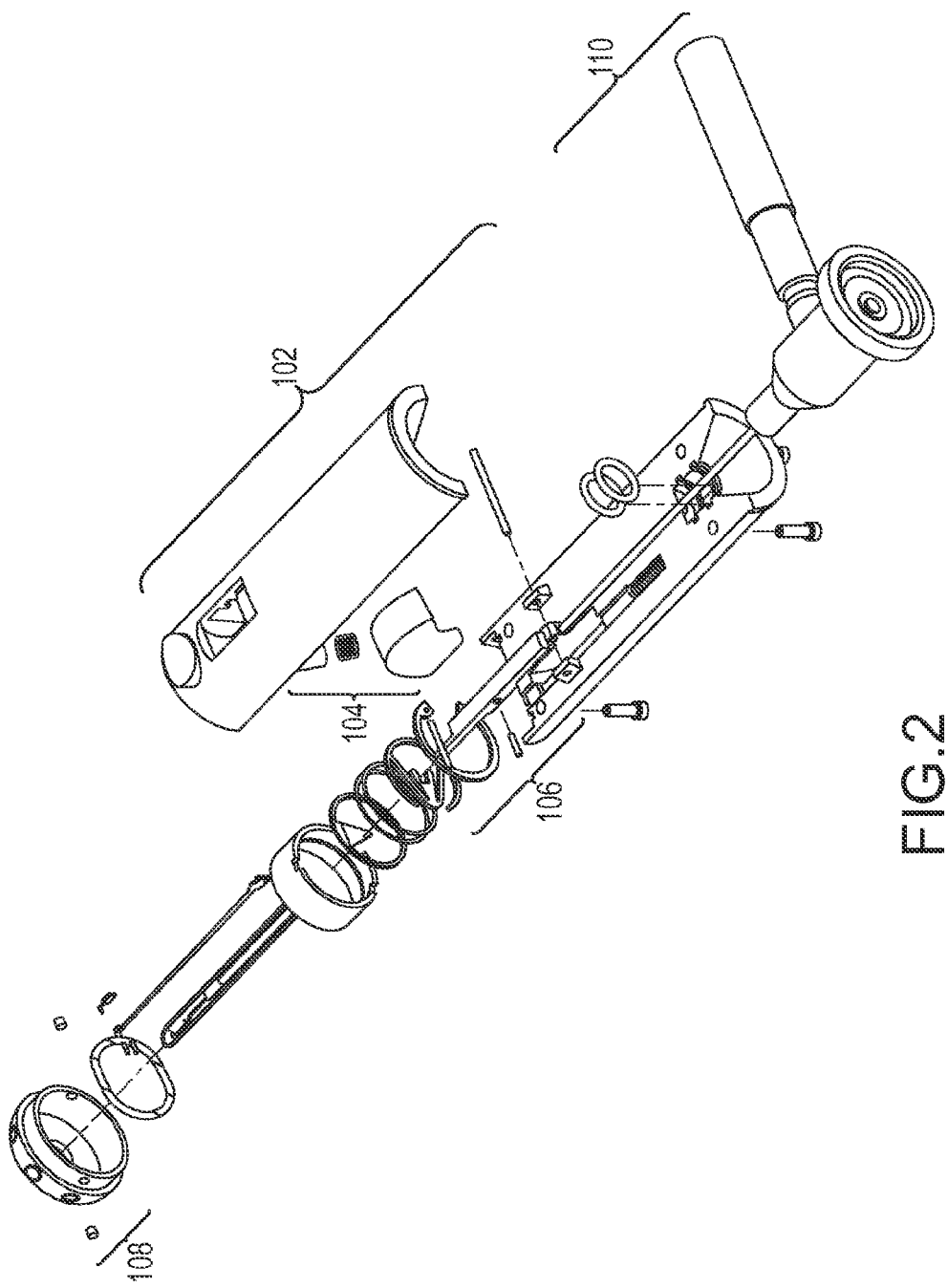
FIG. 2 is an exploded perspective view of the handpiece of FIG. 1.

Referring to FIG. 2, the handpiece 100 of FIG. 1 is shown in an exploded view. The handpiece 100 can include a housing 102 for supporting the several parts of the handpiece. The handpiece can also include an actuation assembly 104 for selectively manipulating the probe and can further include a linkage assembly 106 for mechanically coupling the actuation assembly 104 to the probe. The handpiece can also include a retainer assembly 108 adapted to retain a probe in mechanical communication with the linkage assembly 106. As shown on a proximal end of the handpiece and extending longitudinally there through, a scope assembly 110 can also be provided.

Figure 3:
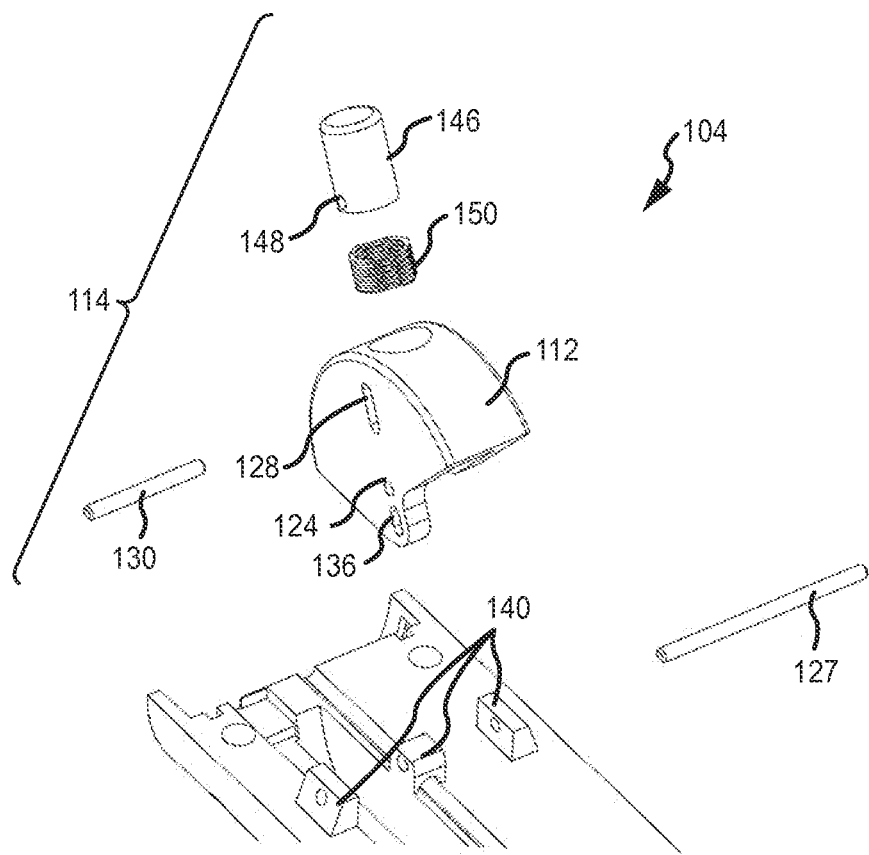
FIG. 3 is an exploded perspective view of an actuation assembly of the handpiece of FIG. 1.

Referring now to FIG. 3, a detailed view of an actuation assembly 104 is shown. The actuation assembly 104 can include a system for inducing translational motion, rotational motion, or a combination thereof. The assembly can include push button assemblies, levers, or sliding elements. Other assembly types can be provided. In the embodiment shown, the actuation assembly 104 includes a pivotal member 112 and a locking assembly 114. The pivotal member 112 is pivotally disposed in the housing 102 and the locking assembly 114 is adapted to selectively secure the pivotal member 112 in one of a plurality of positions.

Figure 4:
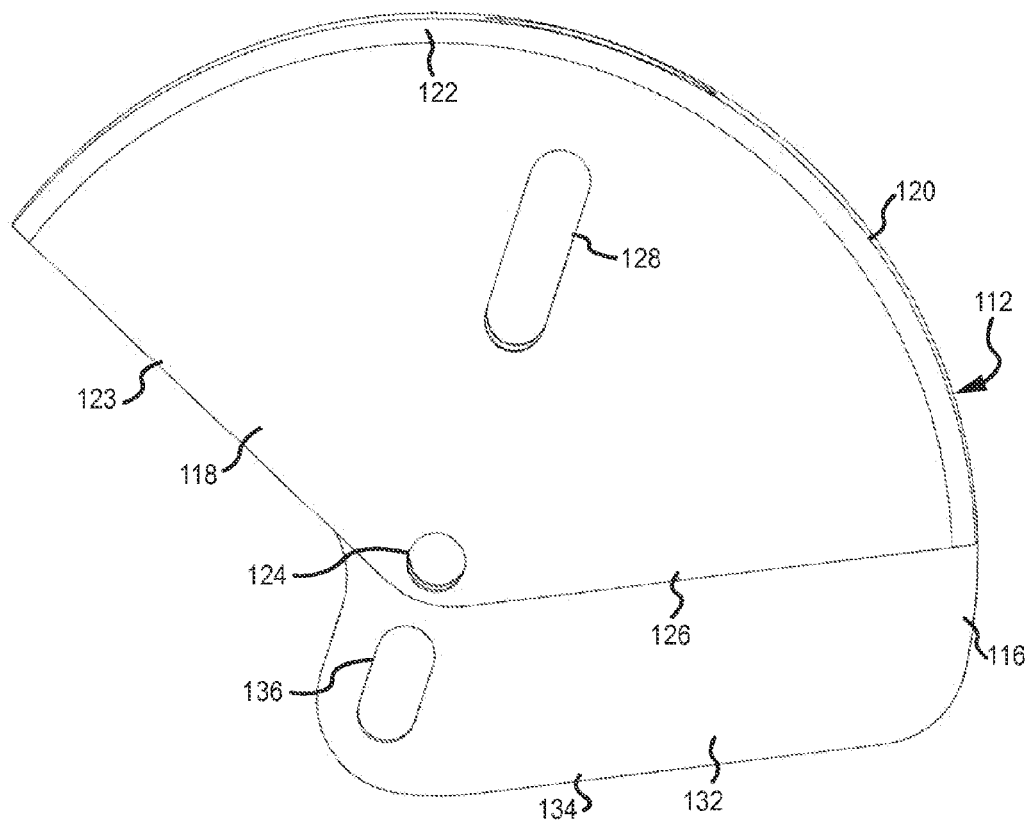
FIG. 4 is a close-up view of a pivotal member of the actuation assembly of FIG. 3.

Referring to FIG. 4, the pivotal member includes a linkage engaging side portion 116, a non-engaging side portion 118, and a selector surface 120 extending there between. As shown, the linkage engaging side portion 116 and the non-engaging side portion 118 each include a relatively planar member resembling a sector of a circle. Each side portion includes an arcuate edge 122 along which the selector surface 120 is connected, the selector surface 120 extending generally orthogonally from the linkage engaging side portion 116 to the non-engaging side portion 118 at any point along the arcuate edge 122. As such, the selector surface 120 can have a generally arcuate shape following the arcuate shape of the arcuate edge 122 of the side portions 116, 118. The non-engaging side portion 118 includes two generally radially extending edges 124, 126. The generally radially extending edges 124, 126 can extend from the center of the arc defined by the arcuate edge 122 or they can be generally aligned with and/or offset from a true radially extending line. The non-engaging side portion 118 includes a pivot hole 124 for receiving a pivot pin 126. The non-engaging side portion 118 also includes a selector pin slot 128 for receiving a selector slide pin 130.

Still referring to FIG. 4, the linkage engaging side portion 116 can be the same or similar to the non-engaging side portion 118, but can also include a linkage engaging tab 132 extending from one of the generally radially extending edges 124, 126. The tab 132 is defined by a continuation of the arcuate edge 122 and a tab edge 134 offset from the generally radially extending edge 124, 126. The tab 132 can include a linkage connecting slot 136 for receiving a linkage actuating pin 138. While multiple arrangements of the mentioned holes and slots can be provided, in the present embodiment the slots and holes in each side of the pivotal member 112 are collinear with the holes and slot in their respective side. The selector slot 128 is positioned between the pivot hole 124 and the arcuate edge 122 and the linkage connecting slot 136 is position opposite the pivot hole 124 from the arcuate edge 122.

Figure 5:
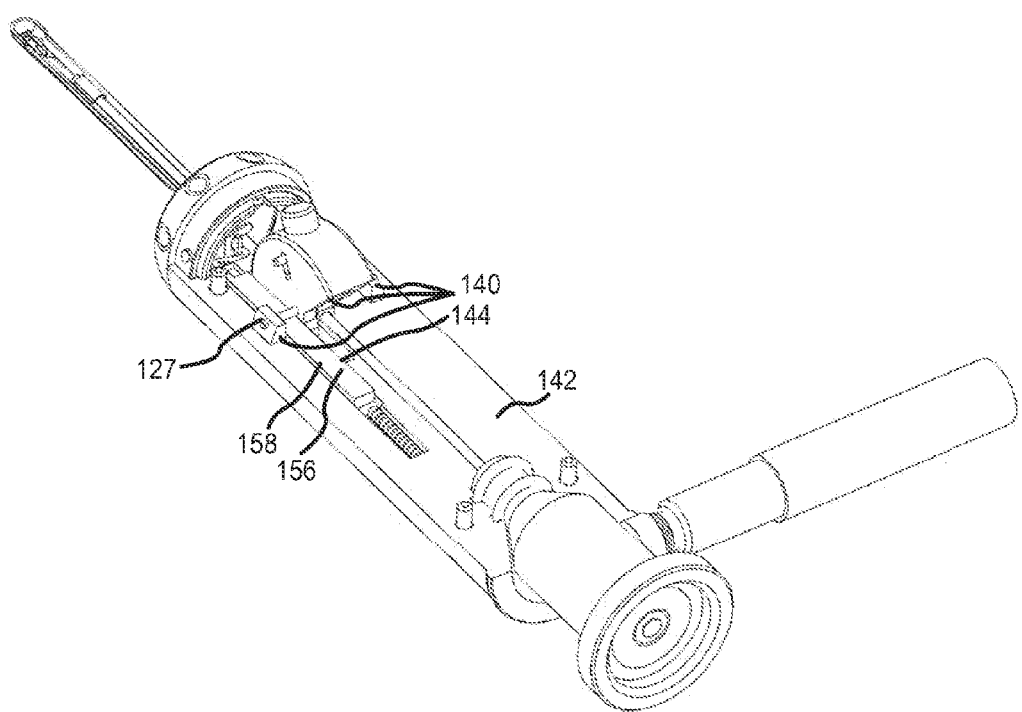
FIG. 5 is a perspective view of the handpiece of FIG. 1 with a portion of the housing removed.

Referring to FIG. 5, the pivotal member 112 shown is mounted within the housing 102 via a pivot pin 126 passing through a series of pin mounts 140 extending from a mating surface 142 of the housing 102. The pivot pin 126 passes through a pin mount 140 on an outboard side of the pivotal member 112, through the pivot hole 124 in the linkage engaging side portion 116 of the pivotal member 112, through another pin mount 140 positioned between the side portions of the pivotal member 112, through the pivot hole 124 in the non-engaging side 118 of the pivotal member 112, and through an additional pin mount 140 on an opposing outboard side of the pivotal member 112. An arcuate trough 144 is provided in the mating surface 142 of the housing 102 to accommodate the arcuate motion of the linkage engaging tab 132 as the pivotal member 112 is pivoted about the pivot pin 126. It is noted that the range of motion of the pivotal member 112 can be limited by the generally radially extending edges 124, 126 of the non-engaging side portion 118 of the pivotal member 112 contacting the mating surface 142 of the housing 102.

A locking assembly 114 can also be provided. The locking assembly 114 can be in the form of a surface slide arranged to slide laterally relative to the pivotal member 112 or longitudinally relative to the handpiece 100 along the surface of the pivotal member 112. Several other locking assembly arrangements can be provided to selectively lock the pivotal member in position.

Referring to FIG. 3, in the present embodiment, the locking assembly 114 is in the form of a push button 146. The button 146 can be generally cylindrically shaped with at least one closed end and can be arranged extending out of the selector surface 120. The button 146 can be arranged to extend generally orthogonally to the selector surface 120 or, alternatively, at an angle thereto. The button 146 can include two selector pin holes 148 arranged on opposing sides of the cylindrical walls of the button 146 and adapted to receive a selector slide pin 130. The locking mechanism 114 can also include a biasing mechanism 150 disposed to bias the button 146 in a direction extending away from the selector surface 120. In the embodiment shown, the biasing mechanism 150 can be in the form of a spring positioned between the pivot pin 126 and the button 146. A slide pin 130 can be provided extending through the selector pin slot 128 in the non-engaging side portion 118 of the pivotal member 112, through the selector pin holes 148 in the button and out the linkage engaging side portion 116 of the pivotal member 112. In this fashion, the button 146 can have a range of motion limited by the sliding motion of the slide pin 130 in the selector pin slot 128 of the pivotal member 112 and the button 146 can be biased toward the position defined by the pin 130 being at the end of the slot 128 most proximate to the arcuate edge 122 of the pivotal 112.

Figure 6:
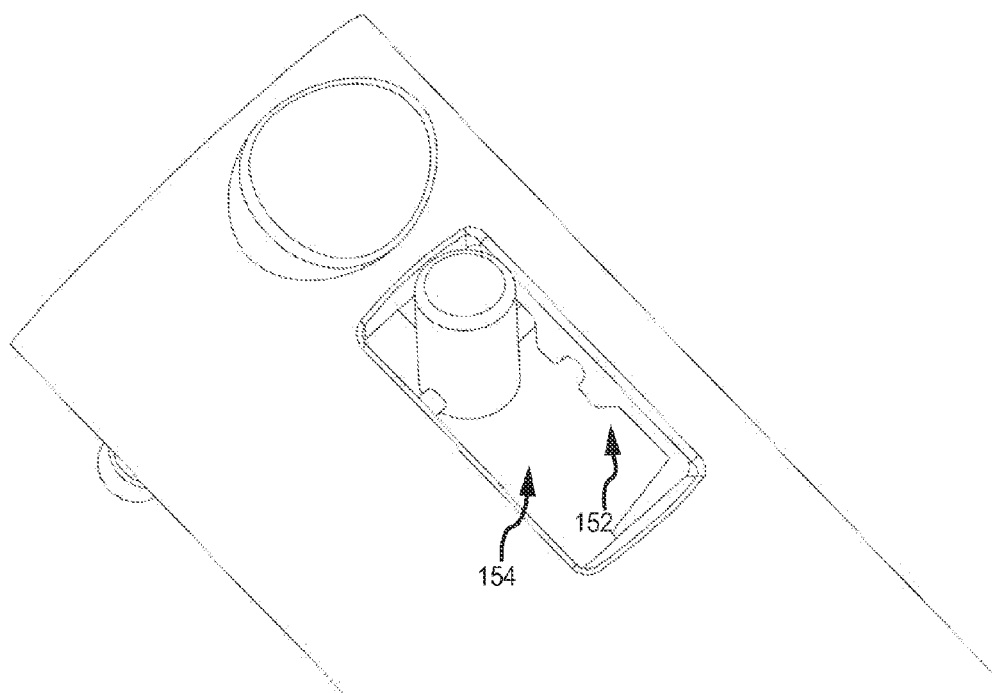
FIG. 6 is a close-up view of a portion of a locking mechanism of the handpiece of FIG. 1.

Referring to FIG. 6, a selector rack 152 can be provided on an inside surface of the housing 102. The pivotal member 112 can extend through an access slot 154 in the housing 102 and the locking assembly 114 can be positioned in the pivotal member 112 such that the slide pin 130 engages the valleys between the teeth of the selector rack 152 when the button 146 is in a non-depressed condition. When the button 146 is depressed against the force of the biasing mechanism 150, the slide pin 130 can move out of the valley between the teeth of the selector rack 152 by sliding in the selector pin track 128 of the pivotal member 112. When the slide pin 130 has cleared the apex of the teeth on the selector rack 152, the pivotal member 112 can be pivoted about the pivot pin 126 to a new location. Upon properly pivoting the pivotal member 112, the button 146 can be released allowing the biasing mechanism 150 to move the slide pin 130 in the biased direction in the selector pin track 128 and into a different valley of the selector rack 152 thereby securing the position of the pivotal member 112.

As mentioned above, a linkage assembly 106 can also be provided. The linkage assembly 106 can include an element or series of elements tying the actuation assembly 104 to the probe. In some embodiments, the linkage assembly 106 can be omitted where motion of the actuation assembly 104 coincides with the desired motion of the probe. The linkage assembly 106 can include a geared system, a pulley system, or a screw system. Other linkage systems 106 can be used and can include several types of motion converting systems.

Figure 7:
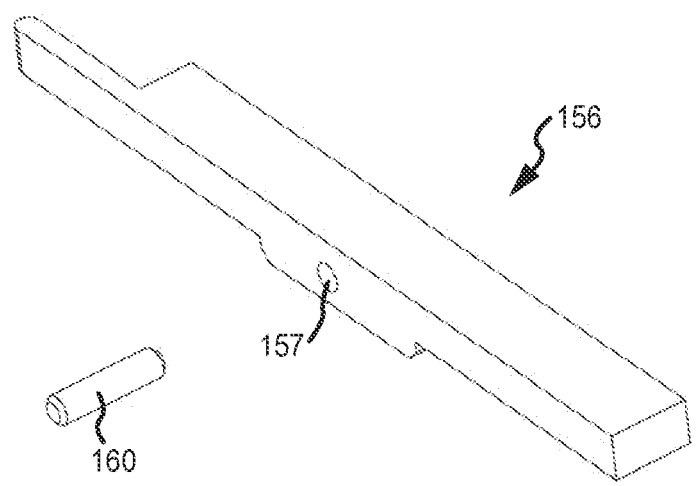
FIG. 7 is a perspective view of a linkage assembly of the handpiece of FIG. 1.

Referring to FIG. 7, the linkage assembly 106 shown is in the form of a slide system. The linkage system includes a linkage member 156 in the form of a generally elongate member with a rectangular cross-section adapted to slide in a track 158. The linkage member 156 includes a thickened region generally near the center of the member with a hole 158 extending therethrough. The linkage member 156 further includes a longitudinally extending member 160 with a narrower cross-section extending from a distal end thereof. The linkage member 156 can be arranged relative to the actuation mechanism 104 so as to convert pivotal motion to translational motion. In the present embodiment, as shown in FIG. 5, the linkage member 156 is positioned within the housing 102 along a lateral side of the actuation mechanism 104. More particularly, the linkage member 156 is positioned adjacent the linkage actuating side portion 116 of the pivotal member 112. The linkage member 156 is positioned in a track 158 provided in the housing 102 that is immediately adjacent to the arcuate trough 144 for the linkage engaging tab 132 of the pivotal member 112. The track 158 can include a recessed portion for the thickened region of the linkage member 156.

Referring again to FIG. 7, the linkage assembly further includes a linkage actuating pin 160. The pin 160 can be positioned in the hole 158 of the linkage member 156 and can extend further into the linkage connecting slot 136 of the pivotal member 112. Accordingly, as the pivotal member 112 pivots about the pivot pin 126, the linkage actuating pin 160 transfers the pivotal motion of the pivotal member 112 to the linkage member 156 causing it to slide in the track 158. In this embodiment, the slotted shape of the linkage connecting slot 136 allows the longitudinal component of the radial motion of the linkage actuating pin 160 to be isolated thereby causing the linkage member 156 to translate solely longitudinally.

The handpiece 100 can also include an auxiliary device. The auxiliary device can include a scope, a light source, an air source, a fluid source, or an electrical source. Other auxiliary devices for assisting in or performing a procedure can be provided. The handpiece 100 can be adapted for use with any one or a combination of these devices.

Figure 8:
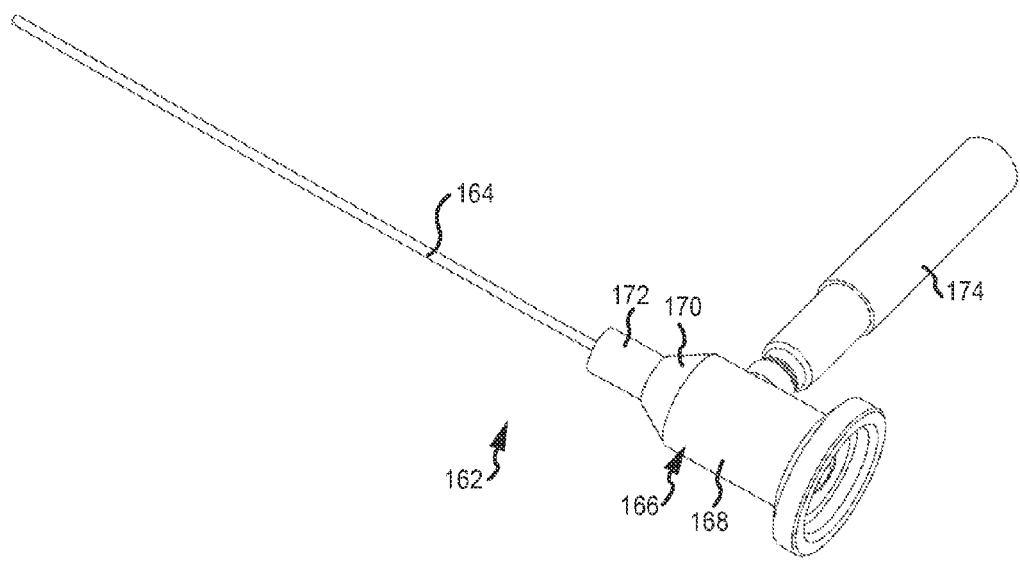
FIG. 8 is a perspective view of a scope and light assembly of the handpiece of FIG. 1.

Referring to FIG. 8, in the present embodiment, the auxiliary device is in the form of a combined scope and light source 162. In some embodiments, the scope and light may be a borescope and coaxial light transmission system. As shown, the scope 162 includes a longitudinally extending scope shaft 164 adapted to extend from a point near the proximal end of the housing 102 up to and beyond a distal end of the housing 102. The distal portion of scope shaft 164 extending beyond the housing 102 is adapted to interact with a variety of probe types and facilitate illumination and viewing of the respective procedure. Accordingly, the scope shaft 164 can, in some embodiments, be in the form of a fiberscope where the scope shaft 164 includes one or more fiber optic cores adapted to shine light into a surgical procedure area and collect images at the distal end of the scope shaft 164 and communicate them to the proximal end where an imaging device may be mounted.

In conjunction with openings and windows provided in the attached probes, the scope and light source 162 can provide 360 deg viewing capability, which can improve the safety of the instrument. When used for a carpel tunnel release procedure, for example, the auxiliary device can allow scope viewing of the instrument, in this case a blade assembly, and the target tissue, in this case the transverse carpel ligament. In other procedures, for example cubital tunnel release, other target structures can be viewed. In addition, simultaneous viewing of other key structures, i.e., the median nerve for carpal tunnel release, can be provided allowing for more safely in transecting the ligament and avoiding injury to the nerve. In this way, while the target tissue is being manipulated, other critical tissue, kept at a distance away from the instrument, can be visually inspected throughout the procedure on target tissue.

Figure 9:
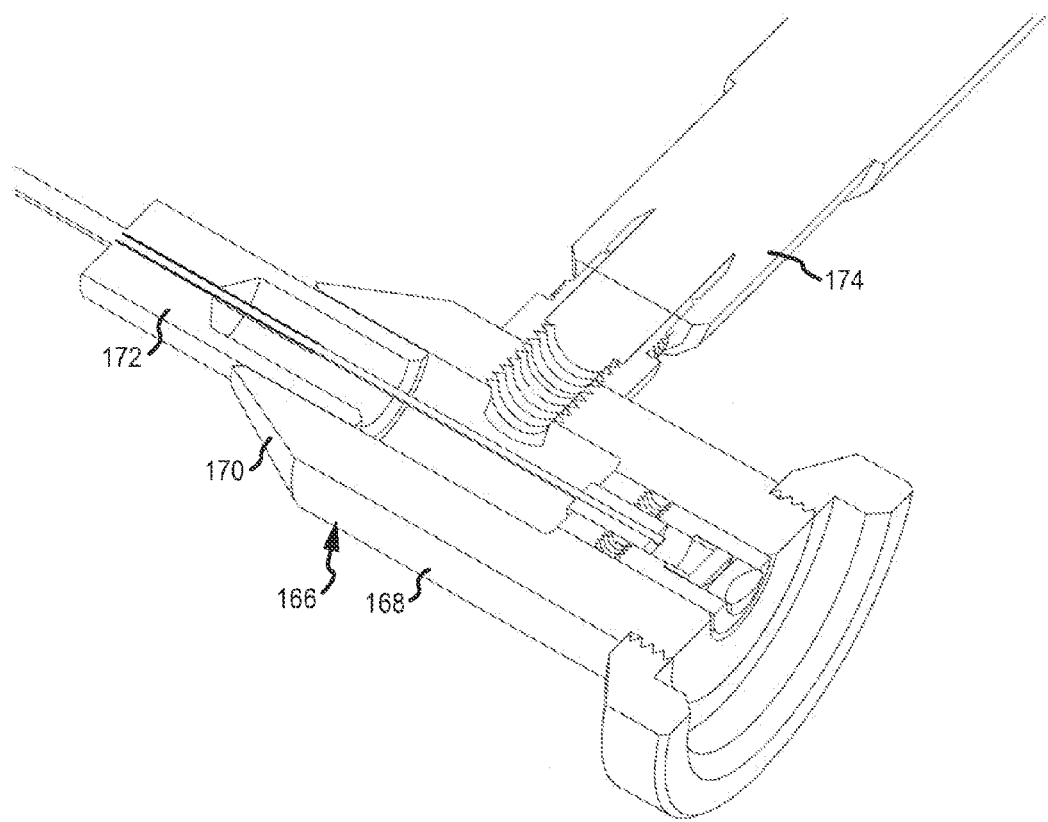
FIG. 9 is a close-up cross sectional view of the scope and light assembly of FIG. 8.

Referring to FIG. 9, at the proximal end of the scope shaft 164 is a junction hub 166. The hub 166 is adapted to receive, at a proximal end, an image collection or imaging device adapted to receive the communicated images from the scope shaft 164. In one embodiment, the hub 166 can be connected to a video camera, which can be connected to a monitor for viewing by the user during a procedure. In a particular embodiment, the camera can be equipped with high definition technology and can display images on a high definition monitor for live viewing by a surgeon or others. The hub 166 can include a generally cylindrically shaped member 168 with a hollow core and a conically shaped insertion portion 170 at a distal end. An additional cylindrically shaped sealing portion 172 can be provided beyond the conically shaped insertion portion 170 and can be adapted to removably engage the housing 102. The junction hub 166 is further adapted to connect the scope shaft 164 to, in this embodiment, a light transmission device 174. The hub 166 can include a threaded coupling on a lateral side of the hub 166 adapted to threadably receive the light transmission device 174. The threaded coupling can include a hollow bore extending therethrough to allow light supplied by the light transmission device 174 to pass into the hub 166 and further be communicated to the distal end of the scope via the scope shaft 164.

The handpiece 100 can also include a housing 102 as mentioned. The housing 102 can be adapted for supporting the several elements of the device. The housing 102 can be a framework with mounts adapted to support each of the elements. In the embodiment, shown, the housing 102 includes a generally solid body with cavities and openings for positioning and arrangement of the elements of the device within the cavities and allowing interaction with the user via the openings.

Figure 10:
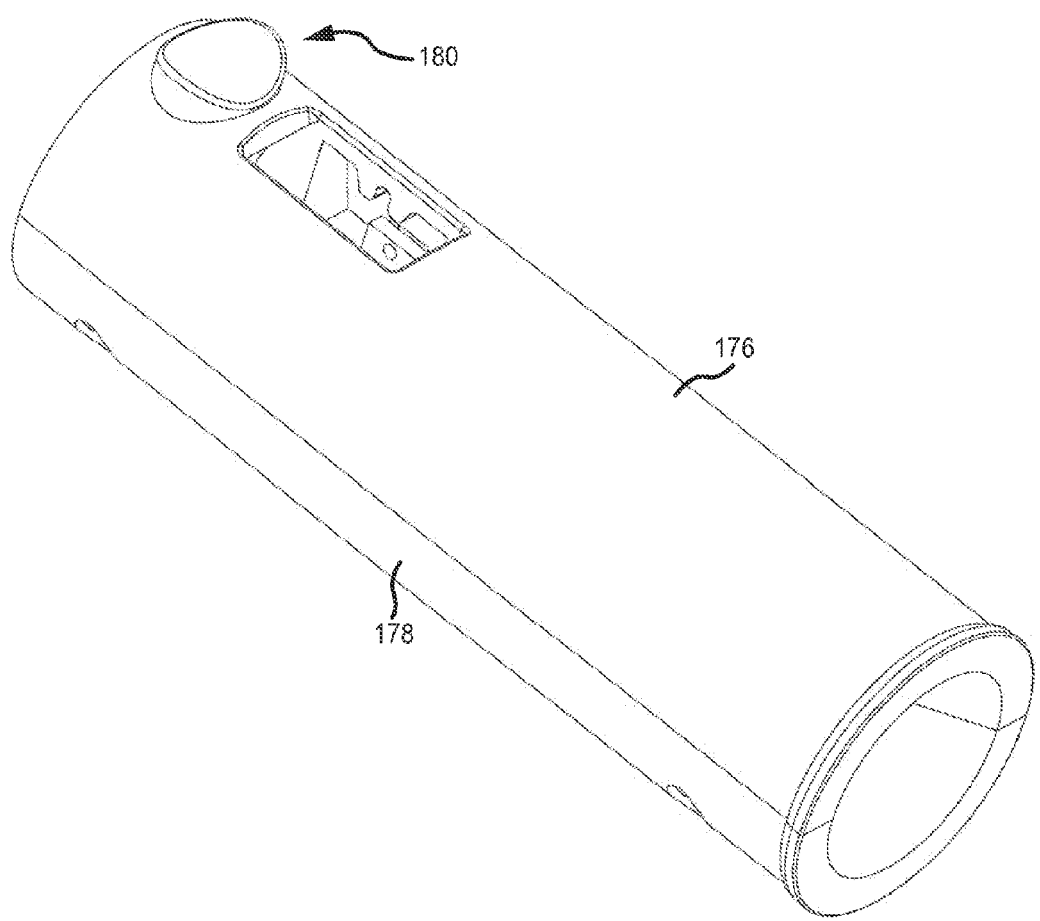
FIG. 10 is a perspective view of a housing portion of the handpiece of FIG. 1.

Referring now to FIG. 10, the handpiece 100 of the present embodiment can include a thumb grip portion 176 and a finger grip portion 178. The thumb grip portion 176 can include a thumb pad 180 adapted for positioning of a user's thumb. The thumb pad 180 can be a raised portion or a recessed portion with a concave surface for tactile and/or ergonomic interaction with the thumb of a user. In the present embodiment, the thumb pad 180 can include a generally elliptically shaped protrusion extending from the surface of the thumb grip portion 176 of the housing 102 forming a raised thumb pad. The surface of the elliptically shaped protrusion can include a concave recess for receiving a user's thumb.

Figure 11:
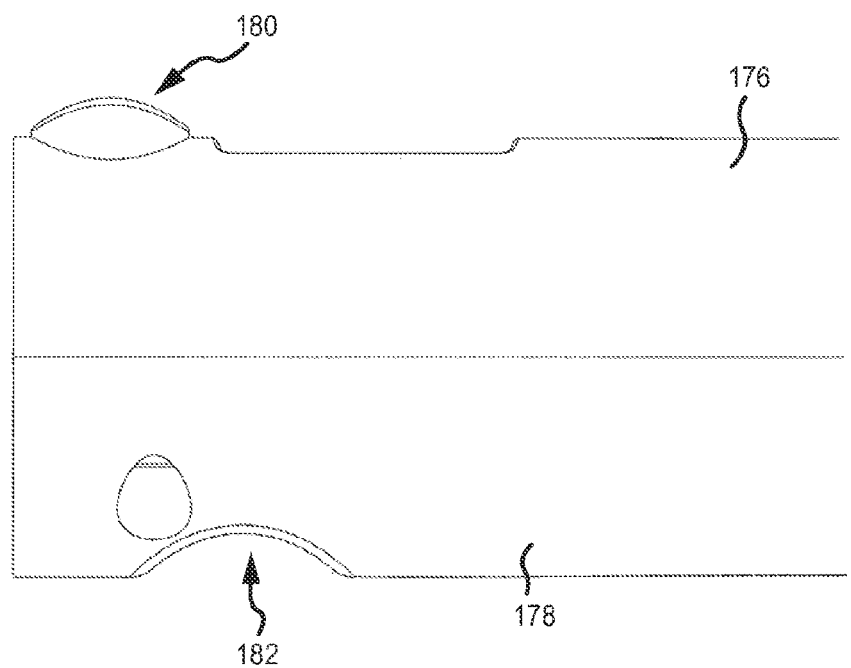
FIG. 11 is a partial side view of the housing of FIG. 10.

Correspondingly, and referring to FIG. 11, the finger grip portion 178 can include a fore finger pad 182 adapted for positioning of a user's fore finger. As with the thumb pad, the fore finger pad 182 can include a raised portion or a recessed portion with a concave surface for tactile and/or ergonomic interaction with the fore finger of a user. In the present embodiment, the fore finger pad 182 can include a recessed portion passing across the surface of the finger grip portion 178 of the housing 102 forming a recessed fore finger pad 182. It will be appreciated that while a fore finger pad 182 alone has been shown in the present embodiment, additional finger pads for the remaining fingers of the hand could also be provided extending proximally along the finger grip portion 178 from the fore finger pad 182.

As shown in FIG. 10, the thumb grip portion 176 and the finger grip portion 178 of the housing 102 can each form a half of a generally cylindrically shaped and generally solid housing 102. A securing arrangement for securing the two portions of the housing 102 together can include one or more threaded bores arranged on the thumb grip portion 176. The threaded bores can be adapted to align with a corresponding number of counter bored holes in the finger grip portion 178 such that fasteners can extend through the finger grip portion 178 and threadably engage the 178 thumb grip portion 176 to secure the finger grip portion 178 to the thumb grip portion 176. The fastening arrangement can be reversed such that the thumb grip portion 176 is secured to the finger grip portion 178. Alternative securing arrangements can be provided such as cylindrical straps or internal snap connections. Other securing arrangements can be provided.

Figure 12:
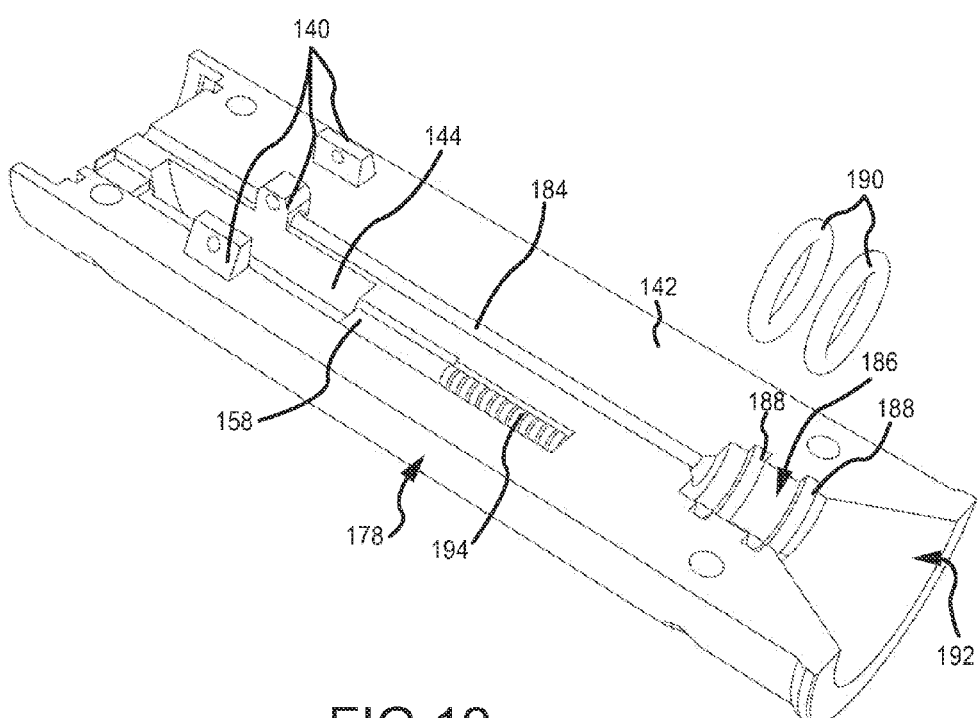
FIG. 12 is a perspective view of a portion of the housing of the handpiece of FIG. 1.

Referring now to FIG. 12, a detailed view of the finger grip portion 178 of the housing 102 is shown. The finger grip portion 178 can have an exterior surface in the form of an outer cylindrical periphery. The finger grip portion 178 can also include a mating surface 142 adapted to engage the thumb grip portion 176. In the present embodiment, the mating surface 142 is generally flat and is adapted to abut a corresponding flat mating surface 143 of the thumb grip portion 176. The mating surface 142 of the finger grip portion 178 can include a series of cavities and/or recesses adapted for arranging several of the elements of the device therein and for guiding the motion of those elements. The mating surface 142 can also include mounting elements adapted to connect elements of the device.

Still referring to FIG. 12, the mating surface 142 can include a longitudinally extending slot 184 adapted to receive half of the scope shaft 164 as it extends through the housing 102. At the proximal end of the slot 184, a cylindrical sealing cavity 186 is provided with a half cylindrical shape. The sealing cavity 186 additionally can include one or more o-ring slots 188 extending along the surface of the cavity. As shown, each o-ring slot 188 can be adapted to receive half of an o-ring 190 adapted to sealably and removably receive the cylindrically shaped sealing portion 172 of an auxiliary device. Extending proximally from the sealing cavity 186 is a conically shaped recess 192 extending to the proximal end of the finger grip portion 178 and adapted to receive the conical portion 170 of an auxiliary device.

As mentioned with respect to the actuation assembly 104, the mating surface 142 of the finger grip portion 178 can also include a series of pin mounts 140. The pin mounts 140 can extend away from the mating surface 142 and include holes adapted to receive the pivot pin 126 of the actuation assembly 104 thereby allowing the pivotal member 112 of the actuation assembly 104 to be secured to the finger grip portion 178. In the present embodiment three pin mounts 140 are provided. Two are adapted to be positioned on an outboard side of the pivotal member 112 of the actuation assembly 104 and one is adapted to be positioned between the side portions 116, 118 of the pivotal member 112. The mating surface 142 of the finger grip portion 178 can also include an arcuate trough cavity 144 adapted to receive the linkage connecting tab 132 of the pivotal member 112. The mating surface 142 can also include a track 158, positioned adjacent to the arcuate trough 144 adapted to guide the motion of the linkage member 156. The track 158 can also include a recessed portion for accommodating the thickened portion of the linkage member 156. Positioned proximal to the track 158, is an additional cavity with a spring block 194 positioned therein. The spring block 194 can include a biasing mechanism adapted to bias the linkage member 156 in a proximal direction. The biasing mechanism can be in the form of a tensioned spring or other device adapted to pull on the linkage member 156 in a proximal direction.

Figure 13:
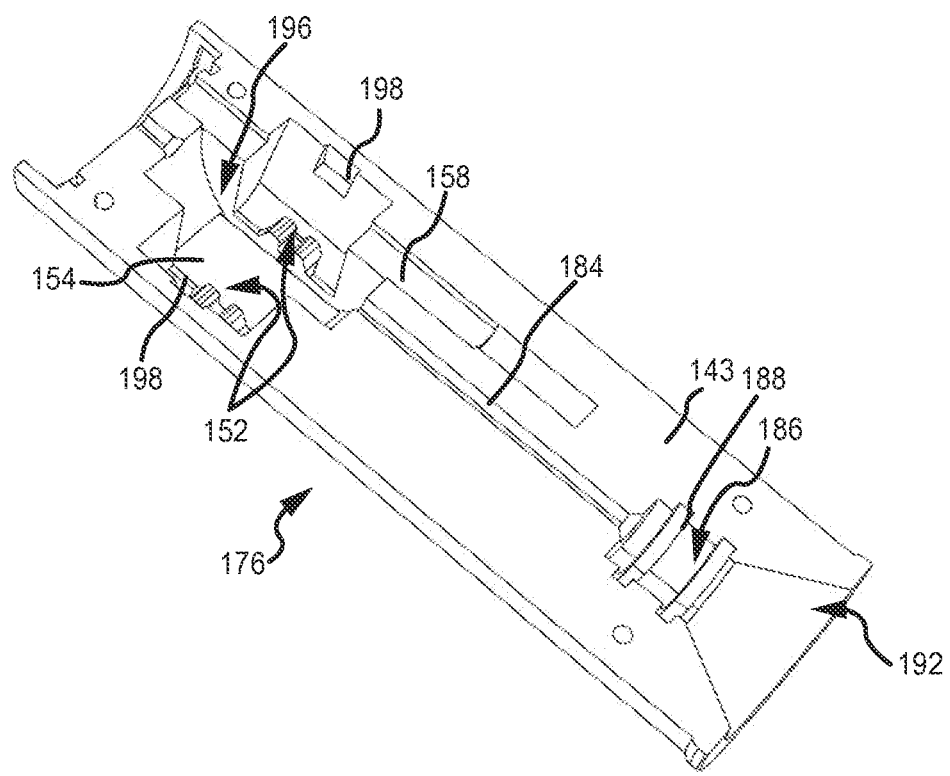
FIG. 13 is a perspective view of another portion of the housing of the handpiece of FIG. 1.

Referring now to FIG. 13, an internal isometric view of the thumb grip portion 176 is shown. The thumb grip portion 176, like the finger grip portion 178 can include an outer surface in the form of an outer cylindrical periphery and can also include a mating surface 143. Like the finger grip portion 178, the thumb grip portion 176 can include a longitudinally extending slot 184, a cylindrical sealing cavity 186 with o-ring slots 188, and a conically shaped recess 192 extending to the proximal end of the thumb grip portion 176. As further shown in FIG. 13, the thumb grip portion 176 can also include a track 158 corresponding to the track 158 in the finger grip portion 178 for receiving and guiding the linkage member 156 therein.

With continued reference to FIG. 13, the thumb grip portion 176 can also include an arcuate trough 196 extending through the full thickness of the thumb grip portion 176 near the mid width. The arcuate trough 196 begins at the mating surface 143 and continues through the thickness of the thumb grip portion 176 creating an access opening 154 in the outer surface of the thumb grip portion 176. As shown in FIG. 13, the arcuate trough 196 can accommodate the pivotal member 112 of the actuation assembly 104 and allow the pivotal member 112 to pivot within the thumb grip portion 176. That is, the arcuate trough 196 can have a radiused surface with a center point the same or similar to a center point of the selector surface 120. The radiused surface of the arcuate trough 196 can be offset from the selector surface 120 of the pivotal member 112 and the arcuate shape of the selector surface 120 of the pivotal member 112 can thus track with the shape of the arcuate trough 196 as the pivotal member 112 pivots. The thumb grip portion can also include pivot pin cavities 198 for receiving the ends of the pivot pin 126 and preventing the pivot pin 126 from translating laterally out of the pivot mounts 140. As discussed with respect to FIG. 6, the thumb grip portion 176 can further include a rack 152 for selectively locking the pivotal member 112 in a desired position.

Figure 14:
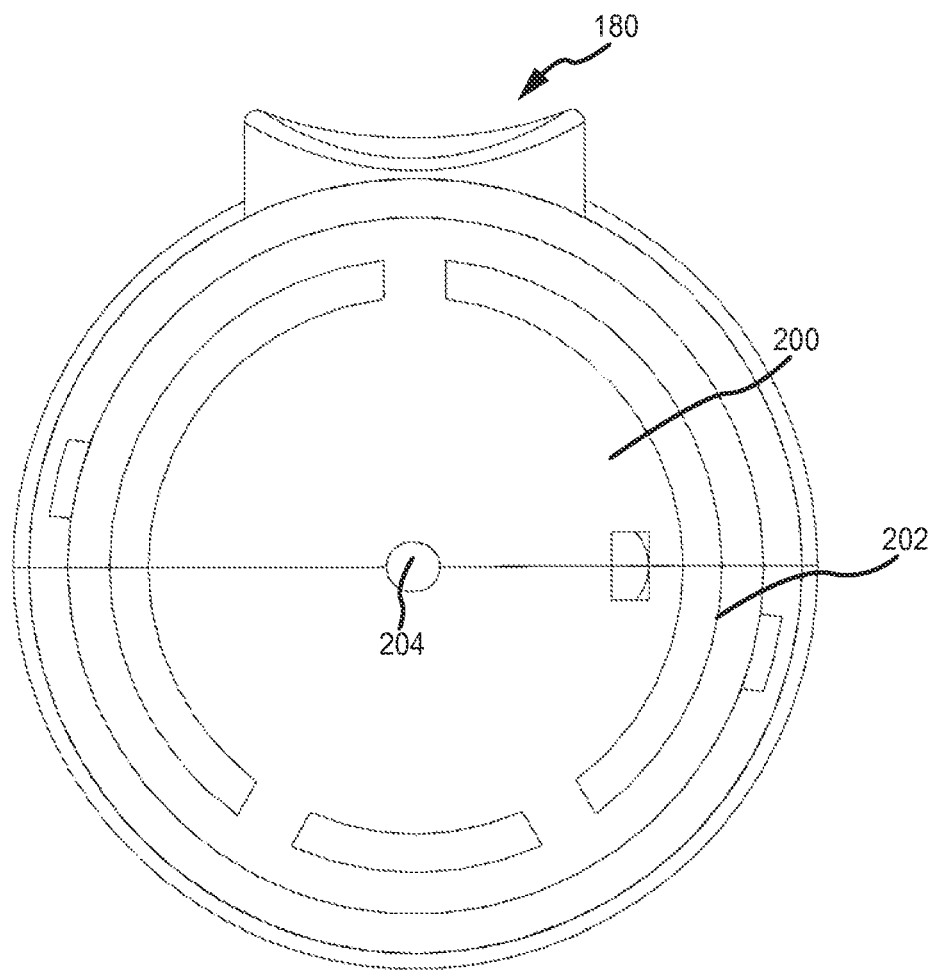
FIG. 14 is a distal end view of the housing of the handpiece of FIG. 1.

Referring now to FIG. 14, a distal end of the housing 102 is shown where the thumb grip portion 176 and the finger grip portion 178 have been assembled to form the housing 102. As shown, the distal end of the housing 102 can include a connection surface 200 adapted for connection of a probe. The connection surface 200 can include an alignment feature adapted for controlling the orientation of the probe. The alignment feature can include one or more or a combination of recesses, protrusions, visual indicators, such as marking lines or color codes, or other aligning elements for alignment with a probe including corresponding aligning elements.

As shown in FIG. 14, in the present embodiment, the alignment feature can be in the form of an annular recess 202 pattern adapted to control the orientation of an attached probe. The longitudinal axis of the housing passing through the connection surface 200 of the housing 102 can form a center point 204 for the annular recess 202. As shown, a line in the plane of the connection surface 200 and passing through the center point 204 will not always cross the annular recess 202 on one side of the point 204 and also cross the annular recess 202 on the other side of the point 204 at exactly the same distance from the point 204. As such, the annular recess 202 is asymmetrical about the longitudinal axis of the housing 102 such that a corresponding annular protrusion can be inserted in a single orientation. The available orientations of an attached probe with an annular protrusion can thus be controlled.

Figure 15:
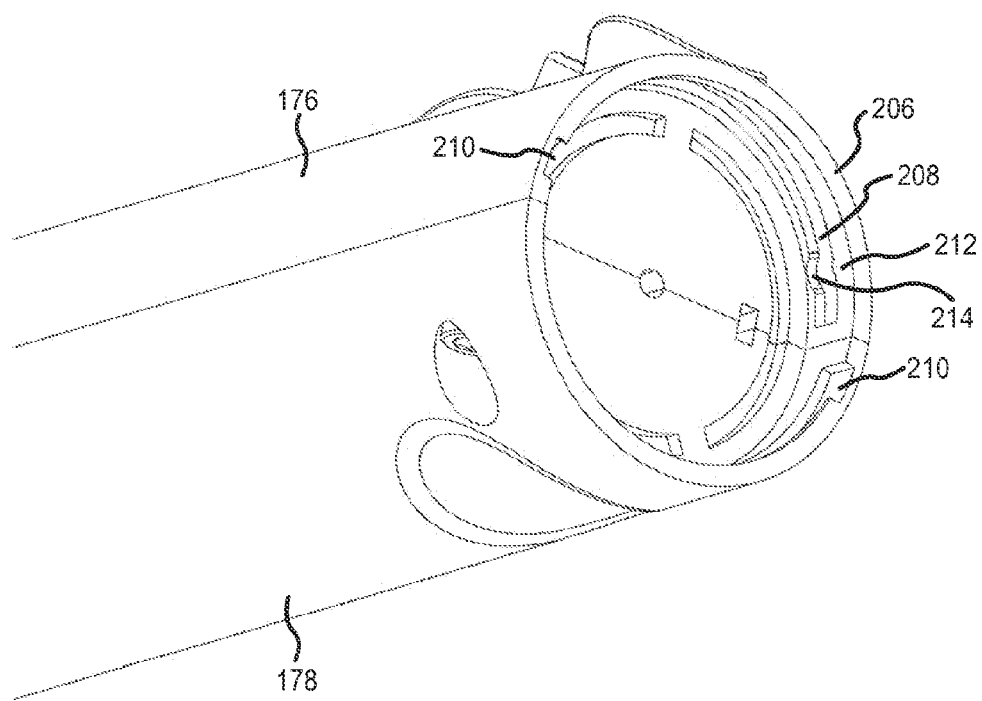
FIG. 15 is a perspective view of the distal end the handpiece of FIG. 1.

Referring now to FIG. 15, a perspective view of the distal end of the housing 102 is shown. As shown, the housing 102 can include a receiving rim 206 extending distally beyond the connection surface 200. The receiving rim 206 can be adapted for connection to a retaining cap 209 positioned over a base of a probe thereby securing the probe against the connection surface 200 of the housing 102. The receiving rim 206 can thus include a connection feature such as a detent arrangement, a female or male thread arrangement, or attachment clips, for example, for attachment of a retaining cap. Other connection features can be included.

As shown, in the present embodiment, the connection feature of the receiving rim 206 can include one or more thread slots 208 extending along an internal facing surface of the receiving rim 206. The thread slots 208 can begin at a distal edge of the receiving rim in the form of an entry slot 210 extending generally longitudinally into the receiving rim 206. The thread slot 208 can then turn and extend generally annularly around the internal surface of the receiving rim 206 and can gradually propagate proximally to form a thread. The thread slot 208 can continue around the internal surface of the receiving rim 206 a partial turn, a full turn, or multiple turns. In the present embodiment, the thread slot 208 extends approximately ½ turn along the internal surface of the receiving rim 206. As shown, in the present embodiment, the receiving rim 206 includes two thread slots 208, one on each ½ of the housing 102. That is, one thread slot 208 is positioned on the thumb grip portion 176 of the receiving rim 206 and another one is positioned on the finger grip portion 178 of the receiving rim 206. The thread slot 208 can also include a setting feature near the end of the thread slot 208 opposite the entry slot 210. As shown, the setting feature can include a bump 212 on one side of the slot 208 and a clearing on a corresponding opposite side of the slot 208. As such, a pin sliding in the slot 208 can pass over the bump 212 via the clearing 214 and motion of the pin in the opposite direction can thus be resisted by the bump 212. 212

Figure 16:
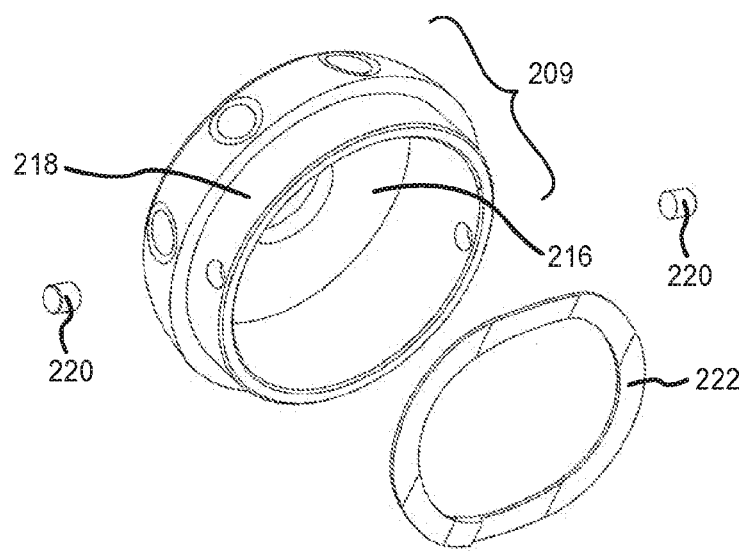
FIG. 16 is an exploded perspective view of a retainer assembly of the handpiece of FIG. 1.

Referring now to FIG. 16, a retaining cap 209 is shown. The retaining cap 209 can be adapted to connect to the housing 102 and retain a probe against the connection surface 202 of the housing 102. The retaining cap 209 can thus be a generally circular member 216 including a connection feature adapted to connect to the housing 102 thereby sandwiching a portion of a probe between the circular member 216 and the housing 102. The circular member 216 can include one or more openings allowing a portion of the probe to extend there through while retaining the remaining portion in secured abutment with the housing 102. The connection feature on the retaining cap 209 can correspond to the connection feature of the receiving rim 206 of the housing 102. Accordingly, the retaining cap 209 can include a detent arrangement, a female or male thread arrangement, or attachment clips, for example. Other connection features can be included In the present embodiment, the connection feature of the retaining cap 209 can include an insertion rim 218 adapted to be inserted within the receiving rim 206 of the housing 102. The insertion rim 218 can be generally annularly shaped and can have an outer radius slightly smaller than an internal radius of the receiving rim 206. The insertion rim 218 can also include one or more cap pins 220. In the present embodiment, the retaining cap 208 can include two cap pins 220, one for insertion into each of the entry slots 210 of the thread slots 208 of the receiving rim 206. The cap pins 220 can be positioned on the insertion rim 218 and can extend radially outward from the insertion rim 218. Accordingly, to secure a probe to the housing 102, the retaining cap 209 can be positioned over a portion of the probe allowing a remaining portion of the probe to extend there through. The insertion rim 218 of the retaining cap 209 can be inserted into the receiving rim 206 of the housing 102 by aligning the cap pins 220 with the entry slots 210 of the thread slots 208. The retaining cap 209 can be advanced such that the cap pins 220 proceed into the thread slot 208 and the retaining cap 209 can then be turned such that the cap pins 220 translate along the thread slot 208 to the bump 212 at the end of the thread slot 208. Additional twisting force can be applied to pass the cap pins 220 past the bumps 212 via the clearing 214 and the bumps 212 can then resist untwisting of the retaining cap 209.

The retaining cap 209 of the present embodiment can also include a cap spring 222 adapted to maintain retaining pressure on the probe and assist in preventing unscrewing of the cap 209. The cap spring 222 can be generally annularly shaped with an out of plane wavy profile. Accordingly, the wavy profile can be pressed toward a flat position when the retaining cap 209 is secured causing the cap spring 222 to bias the retaining cap 209 away from the housing 102 maintaining the frictional resistance of the cap pins 220 in the thread slot 208.

Figure 17:
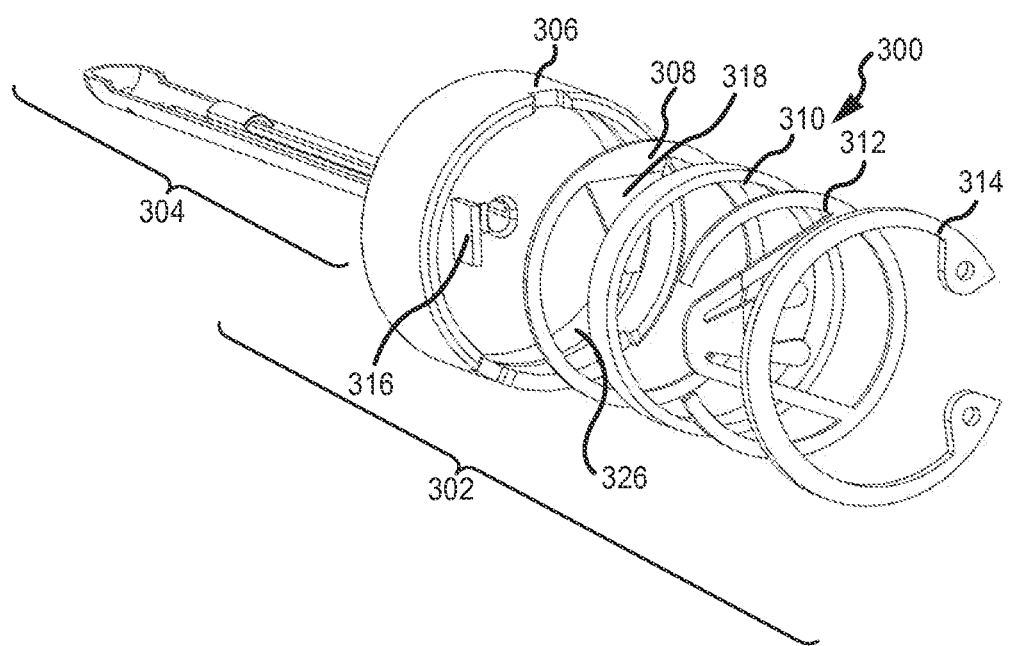
FIG. 17 is an exploded perspective view of a probe adapted for use with the handpiece of FIG. 1, according to certain embodiments.

Referring now to FIG. 17, a first embodiment of a probe 300 is shown. The probe 300 can include a probe base assembly 302 and a procedure assembly 304. The probe base assembly 302 can be adapted to be attached to a handpiece 100 and further adapted to facilitate actuation of the procedure assembly via the handpiece 100. The procedure assembly 304 can be adapted to interface with the base assembly 302 to perform a procedure.

The base assembly 302 can be adapted to be secured to the housing 102 via the retaining cap 209 in sandwiching fashion while providing an interface between the linkage assembly 106 of the handpiece 100 and the procedure assembly 304 of the probe 300. The base assembly 302 can include a stand off member 306, a spring return 308, a spacer ring 310, a motion coupler 312, and a locking ring 314.

Referring to FIG. 17, the stand off member 306 is shown. The stand off member 306 can be adapted to engage the handpiece 100 to define an orientation of the probe 300 and can be further adapted to maintain a working space for the base assembly 302. As such, the stand off member 306 can be in the form of a frame, a shell, or other space defining structure or capsule. Other structures can be provided.

In the present embodiment, the stand off member 306 can be in the form of a cup. The cup can include a circular face for attachment of and extension of the procedure assembly 304 there from. A fulcrum member 316 can also extend proximally from the inside face of the circular face. The cup can include a cylindrical wall extending proximally from the circular face, the circular face and the cylindrical wall forming a cup. The proximal end of the cylindrical wall can include an alignment feature adapted to engage the annular recess 202 in the connection surface 200 of the housing 102. The alignment feature can include notches removed from the proximal end of the cylindrical wall to match the orientation and spacing of the asymmetrical annular recess 202. Accordingly, the proximal end of the cup can be inserted into the annular recess in a single orientation thereby defining the relative orientation of the probe 300 with the handpiece 100.

The cup can have a depth adapted to contain each of the spring return 308, the spacer ring 310, the motion coupler 312 and the locking ring 314. As shown in FIG. 17, the cup can include a locking ring groove 326 extending along the internal periphery of the cylindrical portion of the cup. As such, the spring return 308, spacer ring 310, and the motion coupler 312 can be positioned within the cup and secured therein via the locking ring 314.

Figure 18:
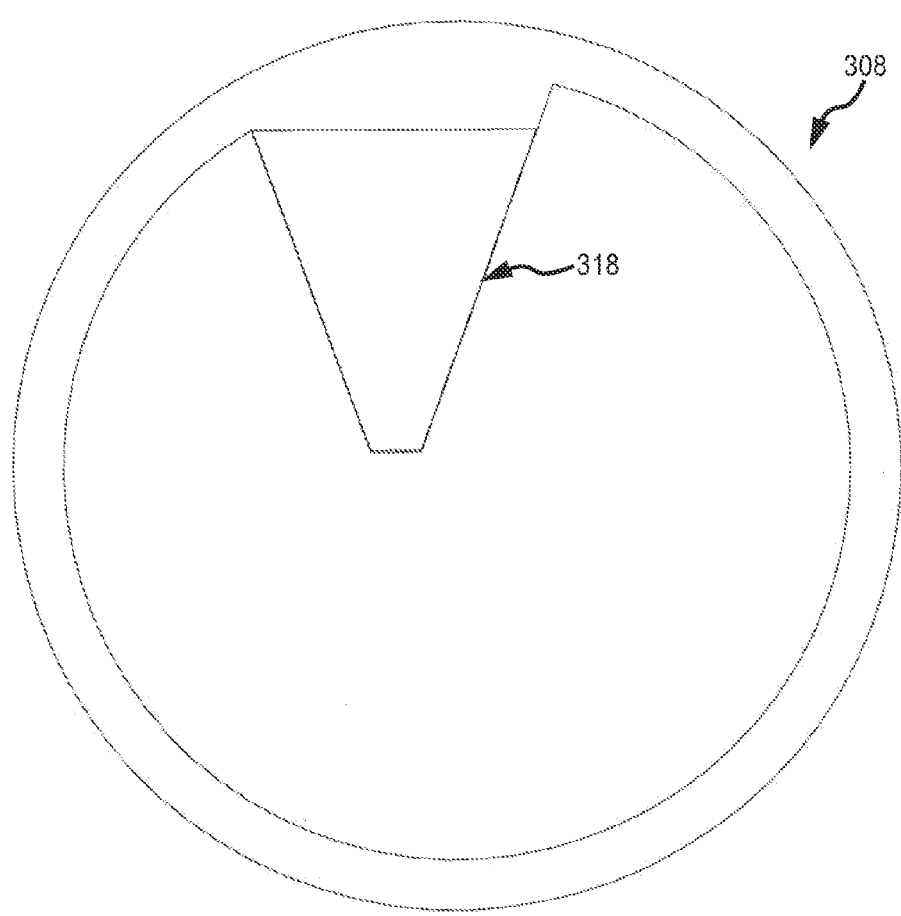
FIG. 18 is an end view of a spring return of the probe of FIG. 17.

Referring to FIG. 18, the spring return 308 can be adapted to be securely positioned within the stand off member 306 and adapted to bias a probe actuator toward a non-actuated position. The spring return 308 can thus be in the form of a spring or other biasing mechanism. In the present embodiment, the spring return 308 is in the form of relatively thin annular disk sized to fit snugly within the cup and be positioned adjacent to the inside face of the circular member of the cup. The spring return 308 can further include a flexing member 318 extending inwardly from the annular ring and adapted to engage a probe actuator. In the present embodiment, the flexing member 318 is generally triangularly shaped with a truncated apex arranged to engage a groove in the probe actuator. As such, longitudinal motion of the probe actuator causes the flexing member 318 to flex due to its engagement in the groove of the probe actuator and the tendency of the flexing member 318 to move toward its non-flexed position accordingly biases the probe actuator.

Figure 19:
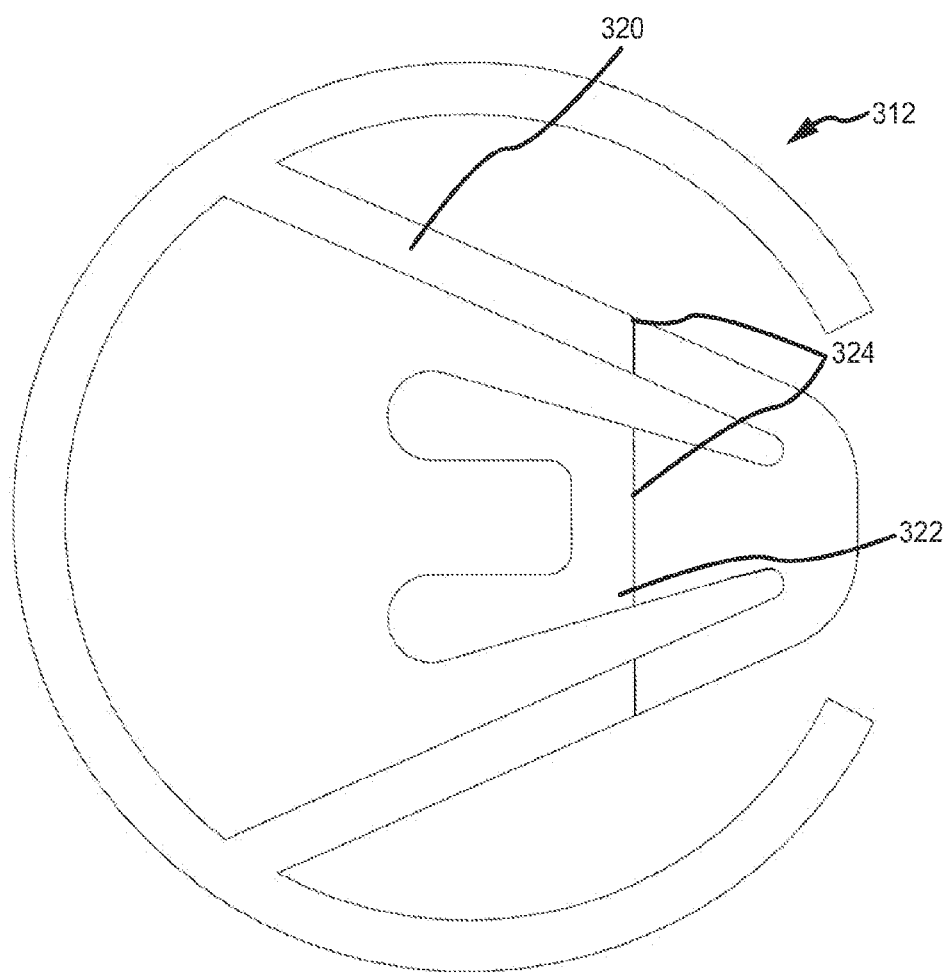
FIG. 19 is an end view of a motion coupler of the probe of FIG. 17.
Figure 20:
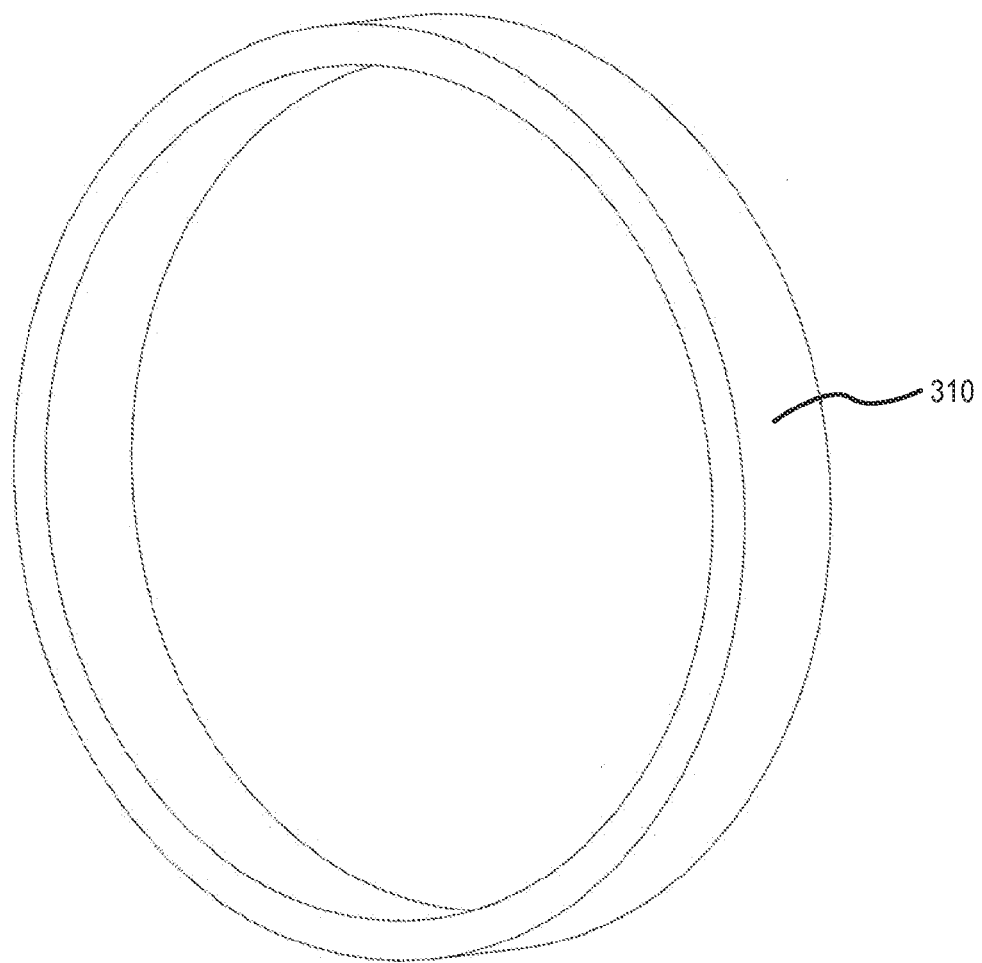
FIG. 20 is a perspective view of a spacer ring of the probe of FIG. 17.

Referring to FIG. 19, the motion coupler 312 can be adapted to be securely positioned within the stand off member 306 and adapted to connect the linkage member 156 to the probe actuator. The motion coupler 312 can thus be in the form of a lever, a button, an extender, or other element adapted to react to the longitudinal motion of the linkage member 156 and cause motion of the probe actuator. In the present embodiment, the motion coupler 312 is in the form of a relatively thin annular disk sized to fit snugly within the cup and be spaced from the spring return 308 by a generally annularly shaped spacer ring 310 shown in FIG. 20. The motion coupler 312 can include a trapezoidal shaped frame 320 extending from the annular disk. The trapezoidal frame 320 can further include an engagement yolk 322 extending into the area defined by the frame 320. The yolk 322 can be adapted to engage the probe actuator. At a point generally midway between the top of the trapezoidal portion 320 and the tip of the yolk 322, a break line 324 can be provided in side elements of the trapezoidal frame 320.

As mentioned, the spacer ring 310 can space the spring return 308 from the motion coupler 312 and can thus be in any form. In the present embodiment, the spacer ring 310 is a relatively thick annular ring adapted to fit within the cup and be positioned between the spring return 308 and the motion coupler 312. The spacer ring 310 can have a longitudinal spacing dimension approximately equal to the length of the fulcrum 316 less the thickness of the spring return 308. Accordingly, when the motion coupler 312 is positioned adjacent the spacer ring 310, the engagement yolk 322 can be positioned generally adjacent to the proximal end of the fulcrum 316.

Figure 21:
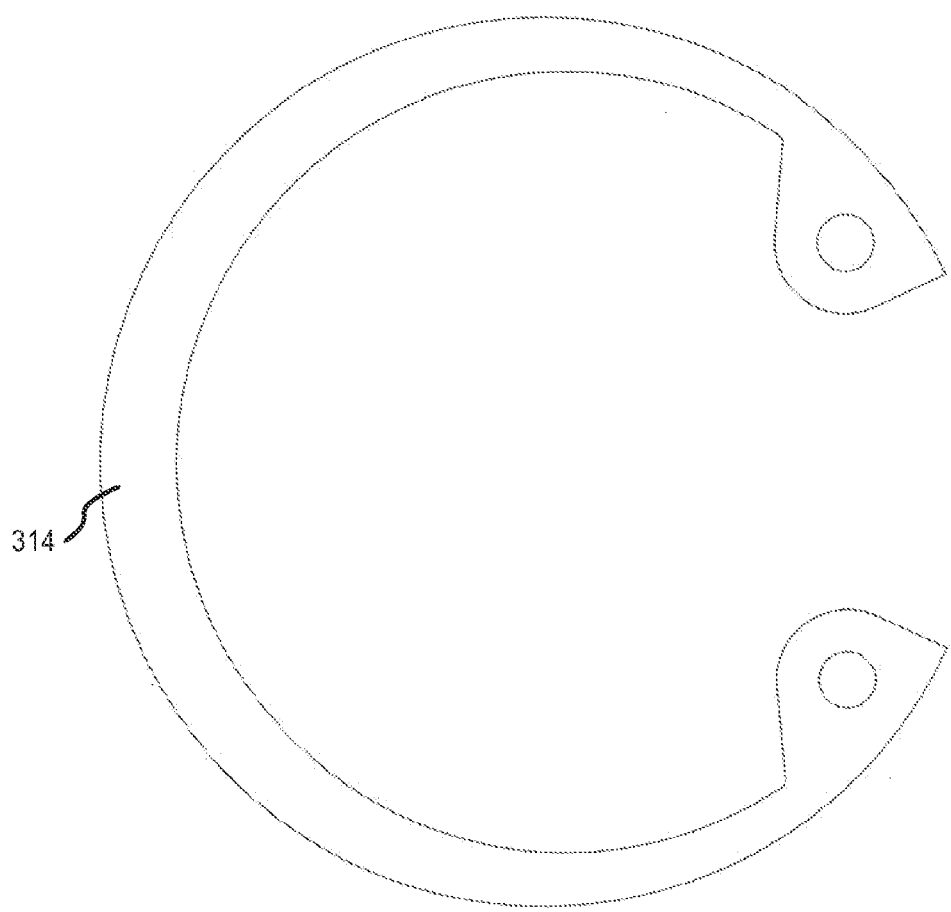
FIG. 21 is an end view of a locking ring of the probe of FIG. 17.

Referring to FIG. 21, the locking ring 314 is shown. The locking ring 314 can be adapted to secure the spring return 308, the spacer ring 310, and the motion coupler 312 within the cup. The locking ring 314 can be adapted to fit within the locking ring groove 326 on the inside face of the cup. As such, the locking ring 314 can be a generally annularly shaped ring with a gap on one side and a diameter slightly larger than the internal diameter of the cup. The gap allows the size of the locking ring 314 to be reduced so as to facilitate insertion of the locking ring 314 into the cup. Positioning the locking ring 314 in the groove 316 releases the locking ring 314 from its reduced size allowing it to expand into the groove 326. The locking ring 314 has an annular thickness sufficient to extend out of the groove 326 and thus sandwich the spring return 308, the spacer ring 310, and the motion coupler 312 between the locking ring 314 and the inside surface of the circular member of the cup.

Figure 22:
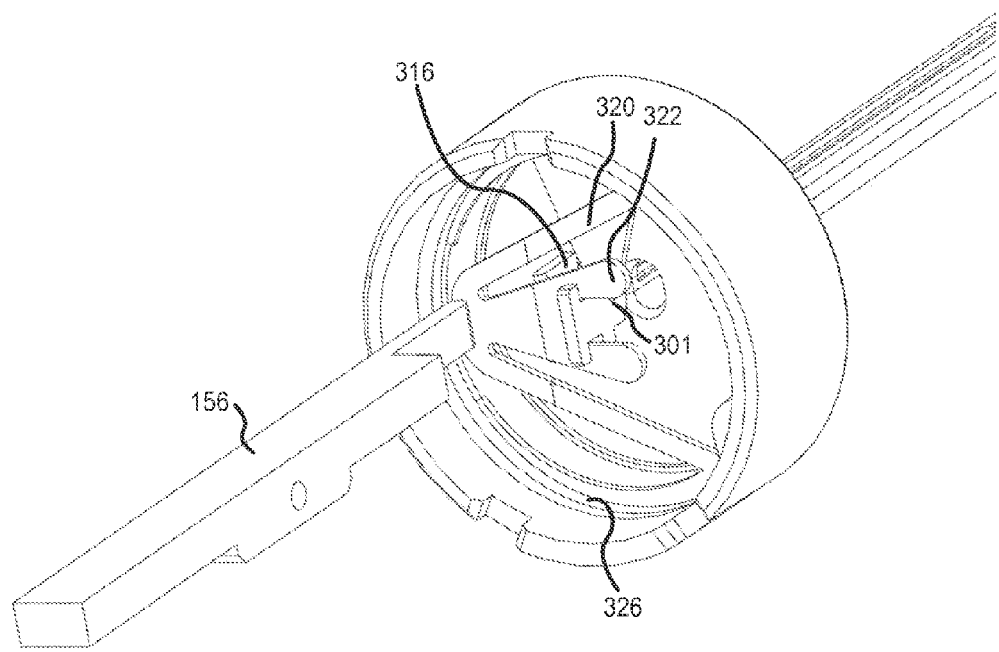
FIG. 22 is a perspective rear side view of the probe of FIG. 17.
Figure 23:
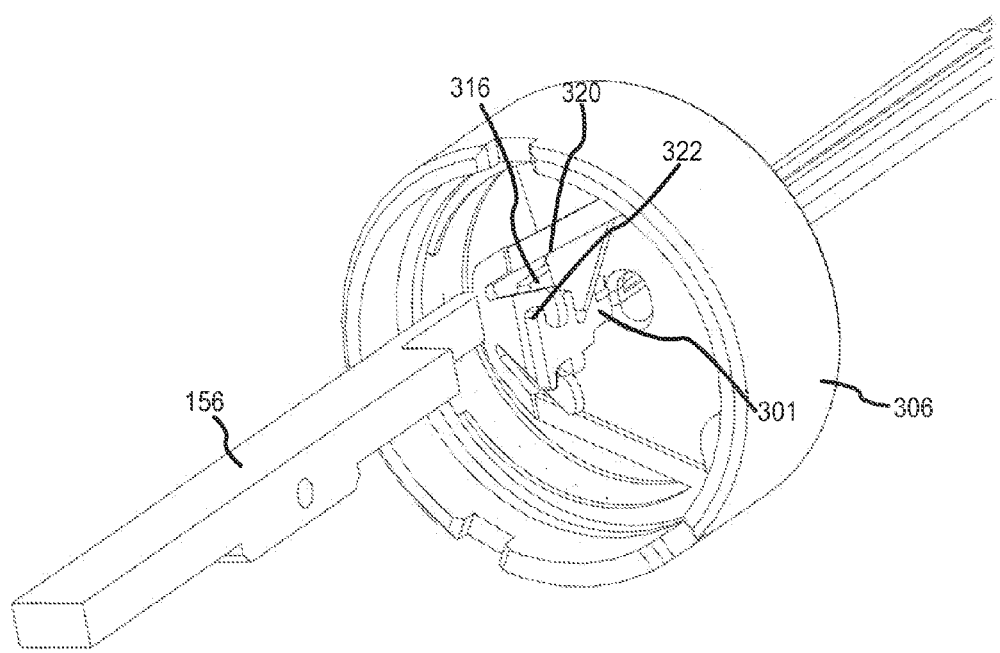
FIG. 23 is a perspective rear side view of the probe of FIG. 17.

Referring now to FIGS. 22 and 23, the functionality of the base assembly 302 will be described. As shown in FIG. 22, the linkage member 156 is positioned proximal to the motion coupler 312. As previously described, actuation of the pivotal member 112 of the handpiece 100 can cause longitudinal motion of the linkage member 156. Accordingly, as shown in FIG. 23, when the linkage member 156 is advanced in a distal direction, it presses on the top of the trapezoidal portion 320 of the motion coupler 312. The motion of the yolk 322 is then resisted by the fulcrum 316 causing the opposing end of the yolk 322 to move in a proximal direction. The breaks 324 in the side elements of the trapezoidal frame 320 can allow for some relative translation of the linkage member without movement of the probe actuator 301. The connection of the yolk 322 to the probe actuator 301 thus causes the probe actuator to also move in a proximal direction.

Figure 24:
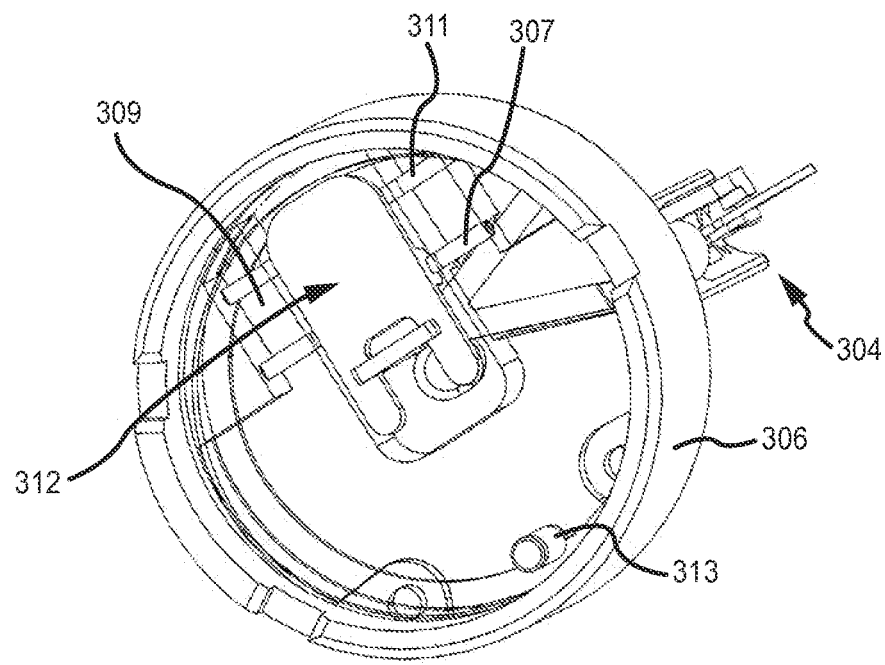
FIG. 24 is a perspective rear side view of a probe according to another embodiment.

Referring to FIG. 24, an alternative embodiment of a motion coupler 312 is shown. In this embodiment, the motion coupler 312 is in the form of a pivot mounted lever. A pivot pin 307 is provided in an insertable disc 309, the disc 309 being adapted to be positioned within the stand off member 306. The disk 309 includes a lever void space and the pivot pin 307 spans across the void space providing a mounting location for the lever. The lever includes a bore for receiving the pivot pin 307 and the lever is pivotally positioned on the pivot pin 307 within the void space of the disc 309. It is noted that the insertable disc 309 can take the place of the spacer ring provided for the previous motion coupler embodiment shown in FIGS. 17-23. The pivot mounted lever includes an engagement yolk adapted to engage the probe actuator 301. The pivot mounted lever is also mounted within the stand off member 306 via the insertable disc 309 such that the portion of the lever opposite the yolk is positioned to be contacted by the distal end of the linkage member 156 and a stop pin 311 is mounted within the stand off member 306 behind this portion of the lever opposite the yolk. As such, the functionality of the motion coupler 312 shown in FIG. 24 is similar to that shown in FIGS. 22 and 23. That is, as the linkage member 156 is advanced distally, the linkage member 156 presses on the lever causing it to pivot about its pivot pin 307 and causing the engagement yolk to move proximally carrying the probe actuator with it. This proximal motion creates a biasing force in the spring return 308 acting on the probe actuator 301 in the distal direction. The motion of the linkage member 156 in a distal direction can be limited by the stop pin 311 positioned distally behind the portion of the lever being contacted by the linkage member 156.

Also shown in this embodiment, a return spring orienting element 313 has also been provided. The orienting element can be adapted to secure the orientation of the return spring 308 so as to prevent the return spring from rotating about the longitudinal axis. The orienting element in this embodiment is in the form of a pin extending proximally from the inside surface of the stand off element 306. The return spring has a corresponding recess for receiving the orienting element on an inside surface of the annular shaped return spring 308. Other shaped orienting elements can be provided including detent relationships, notches, or other elements designed to resist rotation of the return spring. This orienting element can also be provided on the previous embodiment shown in FIGS. 17-23.

Having described the handpiece 100 and at least one example of a base assembly 302 of a probe 300 in great detail, several procedure assemblies 302 of a probe will now be described. The handpiece 100 can be used with one or more interchangeable probes. In the present embodiment, the probe can be interchanged by unscrewing the retaining cap 209, removing and replacing the probe, and replacing the retaining cap 209 and cap spring 222.

Figure 25:
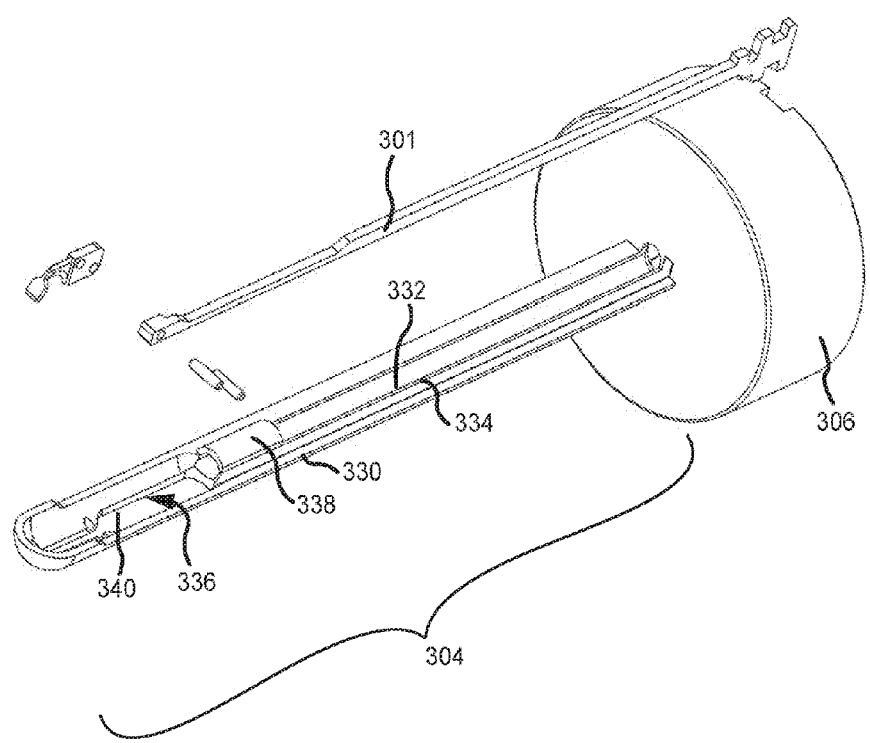
FIG. 25 is a perspective front side view of the probe of FIG. 17.
Figure 26:
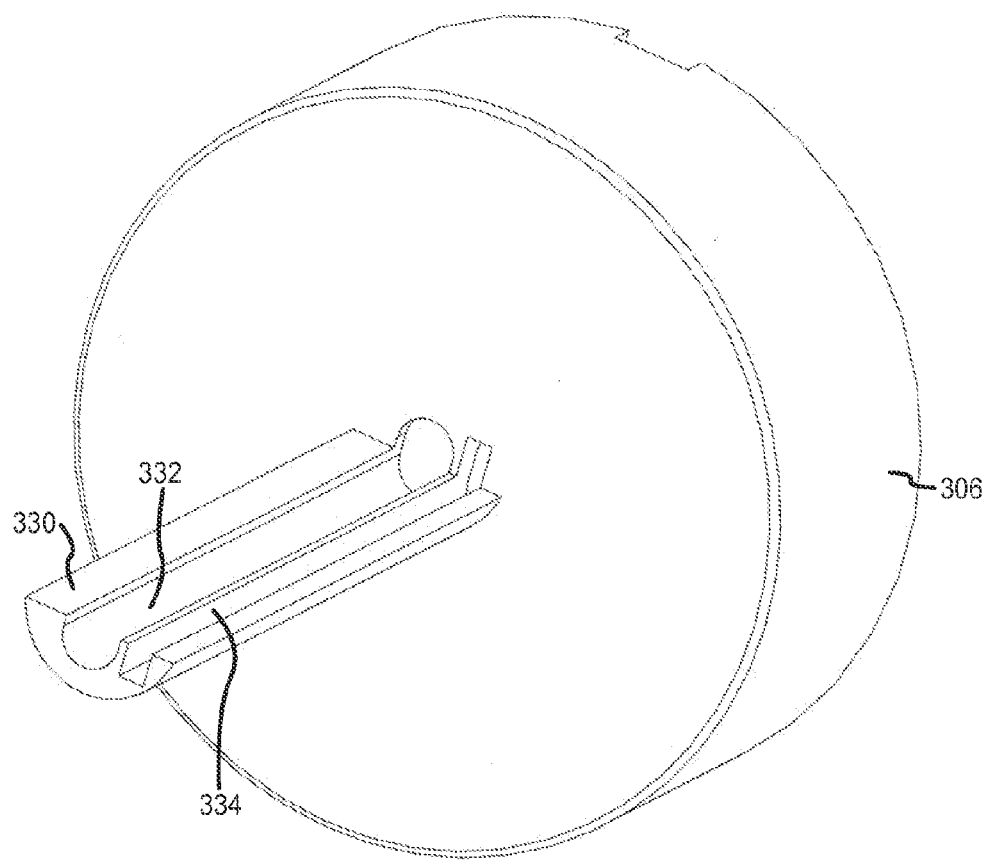
FIG. 26 is a perspective front side view of the probe of FIG. 17 including a cross-sectional view of the insertion member.

Referring to FIG. 25, the procedure assembly 304 of a first embodiment of a probe 300 is shown. As shown, the procedure assembly 302 can include an insertion member 330 adapted for smooth insertion into a surgical site without damaging surrounding structures. The insertion member 330 can be further adapted to hold several devices or elements being used in a procedure. As such, the insertion member 330 can be a generally elongate structure with a smooth outer surface. In the embodiment shown, the insertion member 330 has a semicircular cross-section with an arcuate surface and a working surface. At a distal end, the arcuate surface can turn around the end of the probe to form a semispherically smooth shape. Referring particularly to FIG. 26, the working surface can include longitudinally extending grooves for receiving particular devices. For example, the working surface can include a semicircular groove 332 for receiving the scope shaft 164 and can also include a generally rectangular groove 334 for receiving the probe actuator 301.

The probe actuator 301 can extend from near the proximal end of the procedure assembly 304 to the distal end thereof. The probe actuator can be adapted to transmit actuation forces and/or motions from the actuation assembly via the linkage mechanism to a probe tool at a distal end of the procedure assembly. In the present embodiment the probe tool can be an elongate member nestably positioned in the working surface of the insertion member. The elongate member can be in the form of a shaft, tube, or other elongate structure and it can be slidable in the groove 334. Other cross-section shapes can be provided. While a single member is shown, it can be appreciated that additional longitudinal members can be used to form the probe actuator.

Figure 27:
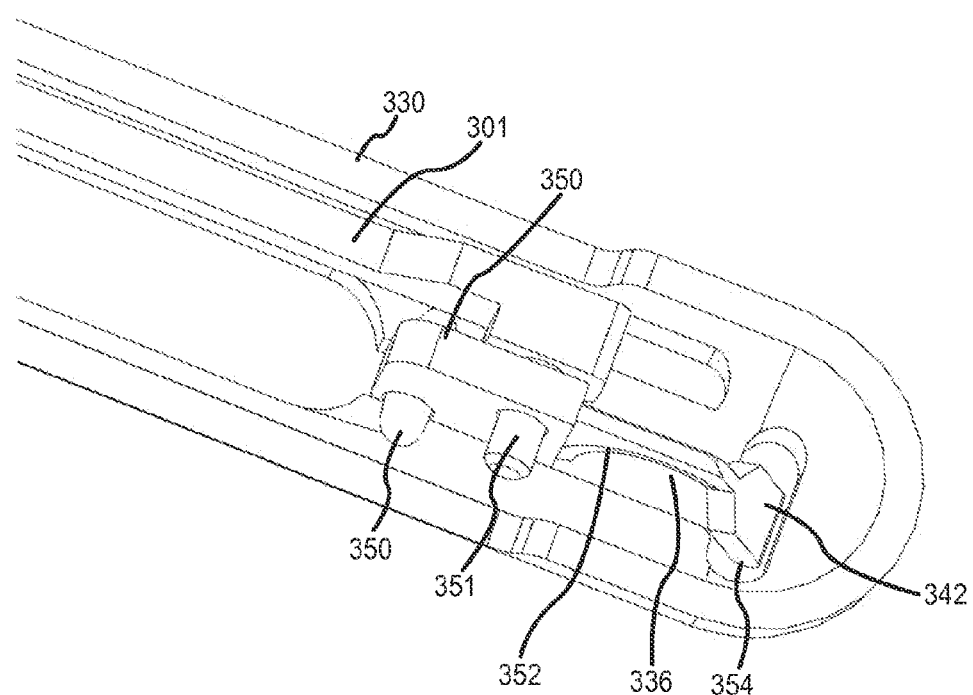
FIG. 27 is a close-up view of the distal end of the probe of FIG. 17.

Referring again to FIG. 25, near the distal end of the insertion member 330, the inside portion of the cross-section of the insertion member 330 can be removed to form a cavity 336. As shown in FIG. 27, the cavity 336 can be adapted to house the distal end of the probe actuator 301 and the probe tool as shown. As also shown in FIG. 25, the insertion member 330 can include a keeper 338 extending over the scope shaft groove 332 for maintaining the scope shaft 164 in place in the groove 332. Also shown is a window 340 in the bottom of the cavity 336 such that anatomical structures can be viewed with the scope 164 on the opposing side of the insertion member 330. This window, in addition to the generally open nature of the insertion member 330 can allow for approximately 360° of visualization allowing target structures and non-target structures to be viewed with the device prior to and during a procedure. For example, during carpal tunnel release, the median nerve can be viewed and avoided and/or protected while dividing or incising the transverse carpal ligament.

Referring again to FIG. 27, a close-up view of the distal end of the probe 300 is shown. The distal end of the probe 300 can house the probe tool, which in this particular embodiment, is a blade 342.

Figure 28:
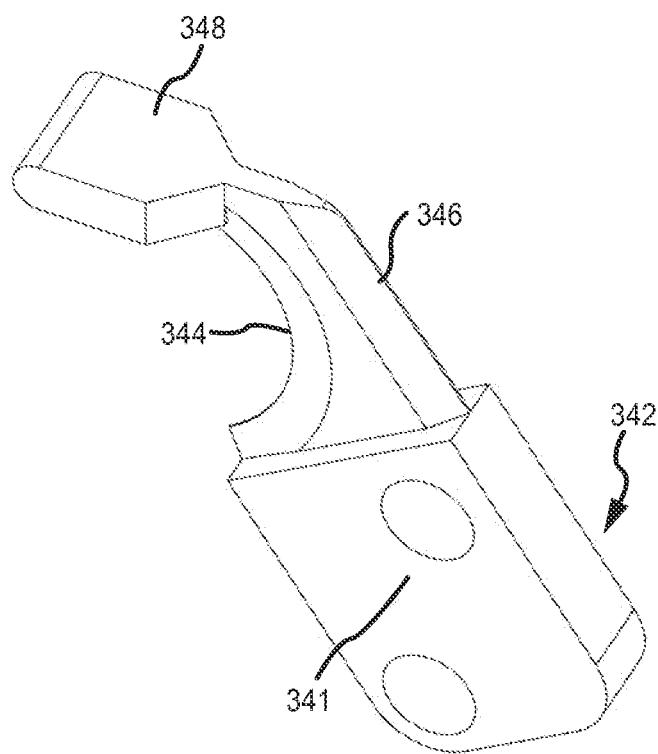
FIG. 28 is a close-up perspective view of a blade of the probe of FIG. 17.

Referring to FIG. 28, the blade 342 can be a generally planar body 341 with two holes for actuation of the blade 342. The blade 342 can include distal and proximal cutting edges 344, 346 extending from the body 341 as shown. The distal cutting edge 344 can have an arcuate shape and the proximal cutting edge 346 can have a relatively straight shape. The blade 342 can also include a transversely extending duckbill portion 348 disposed between the cutting edges 344 and 346 and adapted as a relatively blunt non-cutting edge as shown. The blade 342 can be movable between a non-actuated position and an actuated position and can be positioned at any angle there between. As such, with the blade 342 in a fully actuated position or a selected position in between, the probe 300 can be moved distally and/or proximally (e.g., pushed and/or pulled) to cut tissues with the blade. Additionally, the duckbill portion 348 can be used to grasp loose bodies, tissues, or biopsy specimens, by pinching these things against the insertion member 330 portion of the probe 300. That is, the blade 342 can be in a fully or partially actuated position and the probe can be placed to position a target tissue or loose body between the duckbill portion 348 and the insertion member 330. The blade 342 can then be moved toward the non-actuated position thereby pinching the targeted element between the duckbill portion 348 and the insertion member 330. The duckbill portion 348 can be advantageous due to its blunt non-cutting nature and can function as a leading edge to position the curved cutting portion 344 in the "push" mode. This can be particularly advantageous where the device is used in an supraligamentous approach between the skin and the TCL. In this situation, the duckbill portion 348 portion can be directly adjacent to the median nerve where a smooth blunt non-cutting edge may help to prevent damage to the median nerve.

Referring again to FIG. 27, the distal end of the probe 300 can include a pair of pin sockets 350 for receiving a pivot pin. The distal end can also include a longitudinal concealing slot 352 and a transverse concealing slot 354. The blade 342 can be positioned in the distal end of the probe 300 via a pivot pin positioned in the pin sockets 350. The blade 342 can thus pivot about the pivot pin while remaining anchored in the probe 300. In a non-actuated position, the distal cutting edge 344 of the blade can be positioned in the longitudinal concealing slot 352 and the duckbill portion 348 can be positioned in the transverse concealing slot 354. Additionally, the edges of the distal portion of the probe 300 can taper upward in the vicinity of the blade 342 and extend around the distal end of the probe 300 creating a scoop shaped protective end. The blade 342 can be connected to the probe actuator 301 via an actuating pin 351 connected to the probe actuator 301. As can be appreciated in reviewing FIG. 27, translation of the probe actuator 301 in the proximal direction can cause the blade 342 to pivot about the pivot pin 350 and thus create an exposed condition for the proximal and distal edges of the blade 342.

While a cutting blade type probe has been described, the current handpiece can be used with several different types of probes for diagnostic and therapeutic purposes. For example, the probe can be a retractable needle for use in tissue biopsy procedures or the probe can be in the form of a catheter for the delivery of drugs. Additional procedures can include electrocautery, ultrasound, or laser applications. In addition, the scope can be in the form of scissors, graspers, suction baskets and the like. Additional probe types can be included. The actuation mechanism of the handpiece 100 can be used to elevate one portion of the probe separating it from an adjacent portion thereby opening the device and allowing it to close on a target tissue or object.

Figure 29:
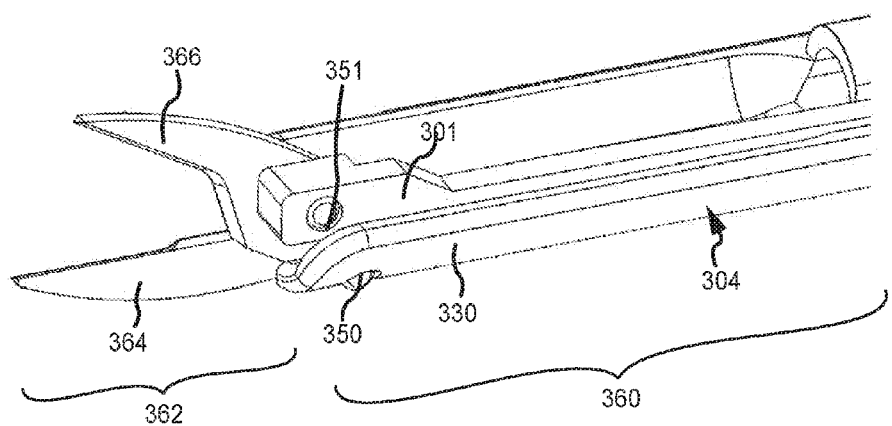
FIG. 29 is a close-up side perspective view of a distal end of a probe according to another embodiment.

Referring now to FIG. 29, a probe 360 with an alternative probe tool is shown. The probe 360 can be the same or similar to the probe 300 previously described and as such, can include a base assembly 302 and a procedure assembly 304 and the procedure assembly 304 can include an insertion member 330. In the present embodiment, however, the probe tool can be in the form of a scissor 362 in lieu of the blade 342. The scissor can include a stationary knife 364 and a pivoting knife 366 mounted on a distal end of the insertion member 330. In contrast to the distal end shown with respect to probe 300, the distal end of the insertion member 330 can include a generally open end allowing the scissor 362 to extend distally therefrom. The insertion member 330 can include a pivot pin 350 the same or similar to the pivot pin 350 in probe 300. The stationary knife 364 can be fixedly mounted on the pivot pin 350 so as to be stationary relative to the insertion member 330. The probe 360 can also include a probe actuator 301 the same or similar to the probe 300 and the probe actuator 301 can include an actuating pin 351. The pivoting knife 366 can be pivotally mounted on the pivot pin 350 and the actuating pin 351. Accordingly, as with the blade 342 described above, the scissor 362 can be actuated via reciprocating proximal and distal motion of the probe actuator 301. That is, as the probe actuator 301 moves proximally, the pivoting knife 366 can pivot about the pivot pin 350 thus opening the scissor 362. The opposite distal motion of the probe actuator 301 can cause the scissor 362 to close. Reciprocating motion of the probe actuator 301 can thus allow for repeated opening and closing of the scissor 362 allowing cutting to be performed.

Figure 30:
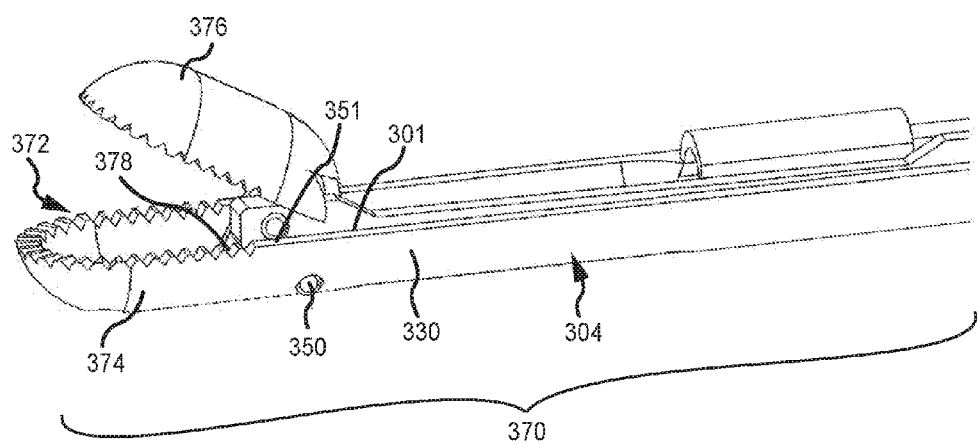
FIG. 30 is a close-up side perspective view of a distal end of a probe according to another embodiment.

Referring now to FIG. 30, a probe 370 with another alternative probe tool is shown. The probe 370 can be the same or similar to the probe 300 previously described and as such, can include a base assembly 302 and a procedure assembly 304 and the procedure assembly 304 can include an insertion member 330. In the present embodiment, however, the probe tool can be in the form of a grasper 372 in lieu of the blade 342. The grasper 372 can include a stationary jaw 374 and a pivoting jaw 376 mounted on a distal end of the insertion member. The distal end of the insertion member 330 in this embodiment can be generally closed with a semi spherical portion similar to that of the probe 300 and forming the stationary jaw 374. In this embodiment, the working surface of the distal end of the insertion member 330 can include teeth extending from the working surface and adapted for interaction with teeth provided on the pivoting jaw 376. The pivoting jaw 376 can include a ½ cylinder shaped portion and a ¼ spherical portion. The ¼ spherical portion can include the teeth mentioned for interacting with the teeth on the stationary jaw 374. The pivoting jaw can include an actuating plate 378 extending into the insertion member 330 and adapted to control the pivoting jaw 376. As with previous embodiments, the probe 370 can include a pivot pin 350 mounted in the insertion member 330 and an actuating pin 351 mounted in a probe actuator 301. The actuating plate 378 can be pivotally mounted on the pivot pin 350 and pivotally secured to the actuating pin 351 such that reciprocating motion of the probe actuator 301 causes the grasper 372 to open and close. The pivoting jaw 376 can also include one or more perforations at a proximal end such that the scope shaft 164 can provide visualization through the pivoting jaw 376 to facilitate grasping of intended structures. The perforation can be in the form of a plurality of holes, slots, or other shapes, or can be a single large hole. In some embodiments, the perforation can be a longitudinal slot such that visualization is not hampered when the pivoting jaw 376 closes but rather that visualization is provided throughout the pivoting motion of the pivoting jaw 376.

Figure 31:
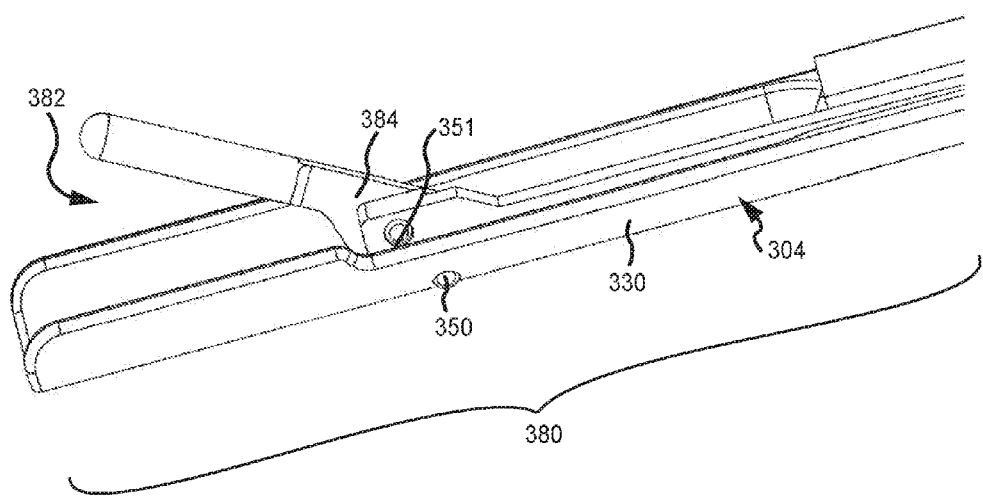
FIG. 31 is a close-up side perspective view of a distal end of a probe according to another embodiment.

Referring now to FIG. 31, a probe 380 with yet another alternative probe tool is shown. The probe 380 can be the same or similar to the probe 300 previously described and as such, can include a base assembly 302 and a procedure assembly 304 and the procedure assembly 304 can include an insertion member 330. In the present embodiment, however, the probe tool can be in the form of a head 382. The head 382 can be relatively elongate and can further take several forms. That is the head 382 can be adapted as a temperature or pressure sensor, a biopsy device, a laser head, an electrocautery head, an ultrasound head, a reservoir for drug delivery and the like. The head 382 can be connected to a catheter or other lumen for fluid, electric, or other communication with the head. In one embodiment, the head 382 can be in the form of a laser. The laser can be positioned to measure blood flow in the target tissue before and then after surgical manipulation. In the case of a carpal tunnel release procedure, this could include measuring the blood flow in the median nerve before and after transverse carpal ligament division. In another application during carpal tunnel release, a catheter can be used to deliver a drug to the median nerve to prevent intraoperative or postoperative adhesions. In some embodiments, the drug can include a hyaluronic acid based substance.

As shown, the head 382 can be relatively elongate and pill-shaped. Other shapes can be provided. The head 382 can be positioned on a connecting plate 384, which can in turn be pivotally supported on a pivot pin 350 and pivotally connected to the probe actuator 301 via an actuating pin 351. In this embodiment, the distal end of the insertion member 330 can be closed or open. As shown, the distal end of the insertion member 330 is open to allow the head 382 to be directed out the distal end of the insertion member 330 in the non-deployed condition. As with the previous embodiments, the pivotal support of the connecting plate 384 allows reciprocating motion of the probe actuator 301 to cause the head 382 to move between the deployed condition shown and a non-deployed condition generally within the insertion member 330.

Figure 48:
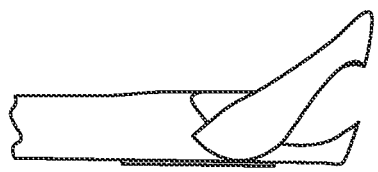
FIGS. 48-50 depict additional probe tool embodiments.
Figure 49:
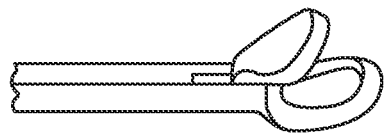
Figure 50:
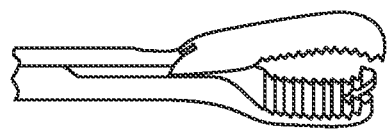

Additional probe tools examples can be adapted for use with the current handpiece 100, for example, those probes available from Smith and Nephews and shown in the Smith and Nephews catalogue in the form of various punches and graspers. For example, as recreated from the Smith and Nephews catalogue, in FIG. 48 a meniscal overbiter punch is shown as an exemplary punch. FIG. 49 is an exemplary oval punch and FIG. 50 is an exemplary grasper. These devices can be actuated via a reciprocating motion that can be adapted for actuation by the probe actuator of the probe described above.

To facilitate use of different probes, a cannula 101 can also be provided that is adapted to sleeve over the probe. As shown best in FIG. 1, the cannula 101 can have an annular cross-section and can be sleeved over the probe prior to first insertion. The cannula 101 can have a length less than that of the probe such that the cannula 101 can slide distally and proximally along the length of the probe. Once inserted, the cannula 101 can be slid in a proximal direction to expose a blade or other probe tool on a distal end of a probe such that the probe can interact with target tissues. When a different probe is needed, the cannula 101 can be slid distally over the probe and left in place while the probe is removed. The cannula 101 can thus act as a place holder while a probe is removed from the handpiece 100 and replaced with a new probe. Upon replacement of the new probe, the handpiece can be used to reinsert the probe into the procedure site and the cannula 101 can again be slid proximally to expose the tool at a distal end of the newly placed probe. In some embodiments, the cannula 101 can be a clear cannula to facilitate viewing of the probe position, via a scope, relative to target structures when the probe is advanced through the cannula 101.

Figure 32:
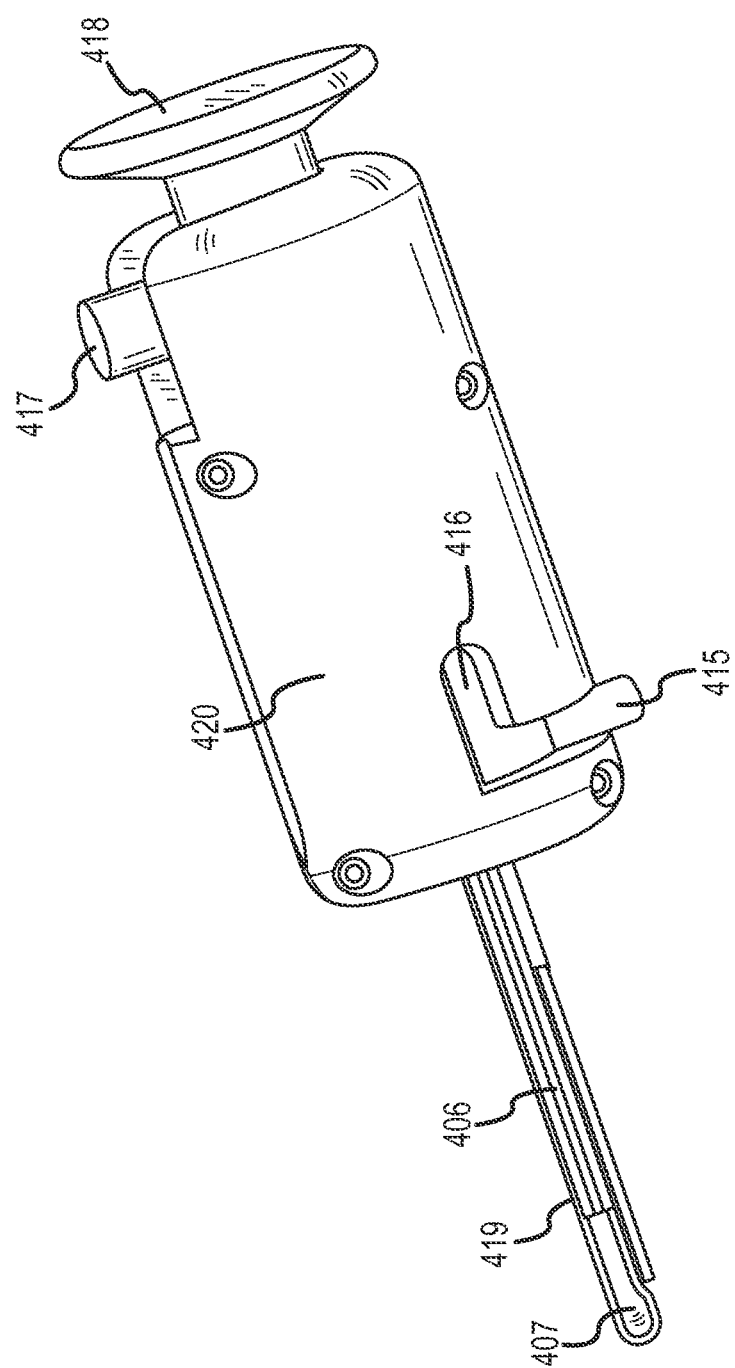
FIG. 32 is a perspective view of another embodiment of a handpiece and probe.

Having described a first embodiment of a handpiece and a series of probes, additional handpieces and probes will now be described. FIG. 32 shows a reuseable handpiece portion 420 of an instrument attached to a probe 419 with a cutting blade 407 on the distal end of the probe 419. The handpiece portion 420 has an actuator knob 415 that can be moved and locked in position inside a cutout groove 416 in the body of the handpiece 420. In some embodiments actuation of the knob 415 is used to manipulate the position of the blade 407. The probe 419 may include an endoscopic visualization system 406 that extends along the probe 419. The endoscopic visualization system 406 may include a first fiber optic cable that acts as a light source conduit for illuminating the surgical site and a second fiber optic cable or other endoscopic camera system that acts as a camera conduit through which the surgical site may be viewed. This system can be the same or similar to the scope and light device 162 described above or it can be different. The handpiece body 420 may include a light source inlet 417 and a camera connection coupling 418. The light source inlet 417 may couple a light source to the handpiece body 420, the light source 417 thereby being able to communicate light to the first fiber optic cable of the visualization system 406 to illuminate the surgical site. Similarly, the camera connection coupling 418 may be used to couple a camera system to the handpiece body 420, the second fiber optic cable of the visualization system 406 thereby being able to provide visualization of the surgical site to the camera system.

Figure 33:
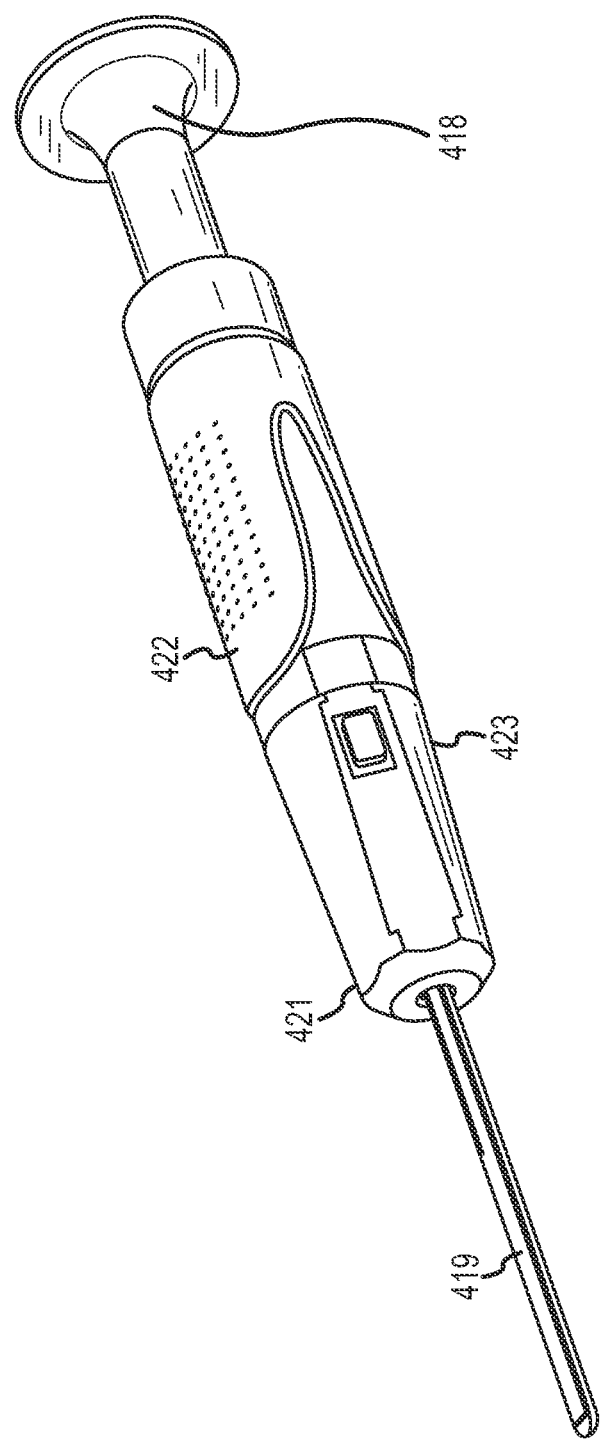
FIG. 33 is a perspective view of another embodiment of a handpiece and probe.

FIG. 33 shows one embodiment of a finished exterior of the reuseable handpiece portion of the instrument attached to a disposable probe 419. The handpiece comprises a first gripping region 422 for the palm, a second gripping region for the thumb and finger(s) 421, and an actuator button 423 that inserts and maneuvers elements on the distal end of the probe 419.

Figure 34:
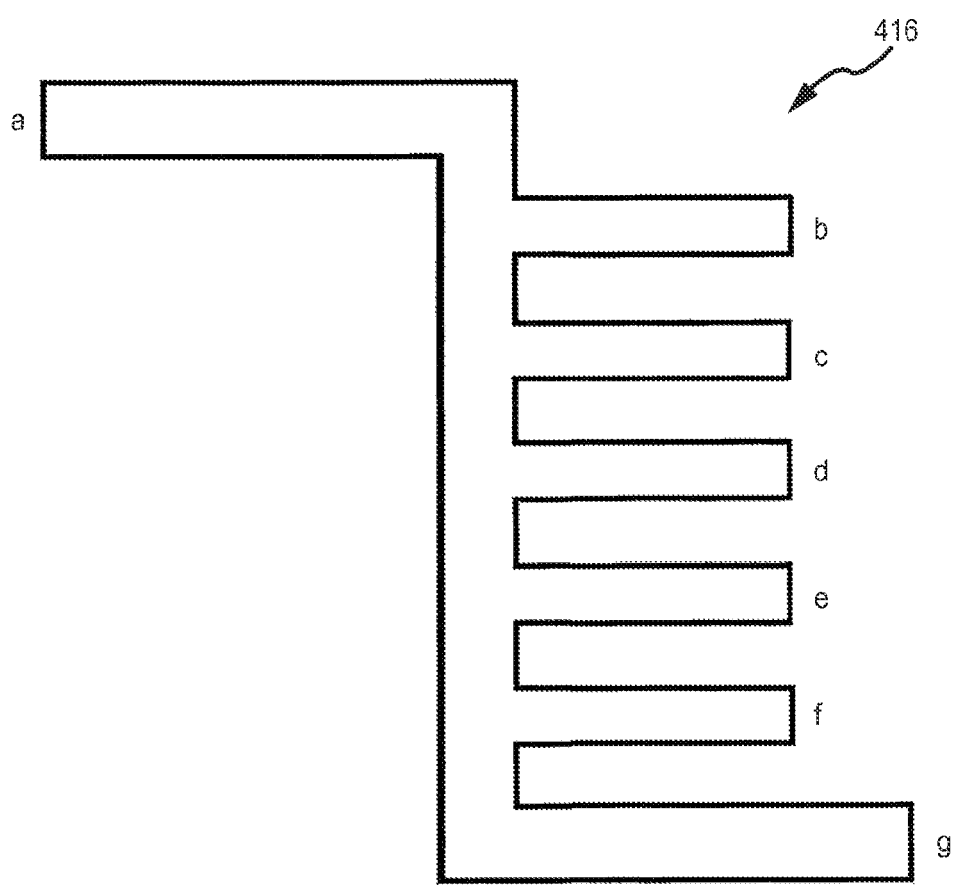
FIG. 34 depicts a travel pathway of a knob for use in manipulating a probe.

FIG. 34 shows an alternative design for the cutout groove 416, as shown in FIG. 28, in which the knob moves and locks to actuate an element on the distal end of the disposable probe. The exact object controlled by the actuator knob depends on the purpose of the probe. In one embodiment, when the probe has a cutting blade the knob can be moved to extend and change the angle of the blade. When the knob is locked in position (a) the blade is retracted. When the knob is locked in position (g) the blade is fully extended at 90 degrees. When the knob is locked in intermediate positions the blade is between 0 and 90 degrees: (b) 15°, (c) 30°, (d) 45°, (e) 60°, and (f) 75°.

Figure 35:
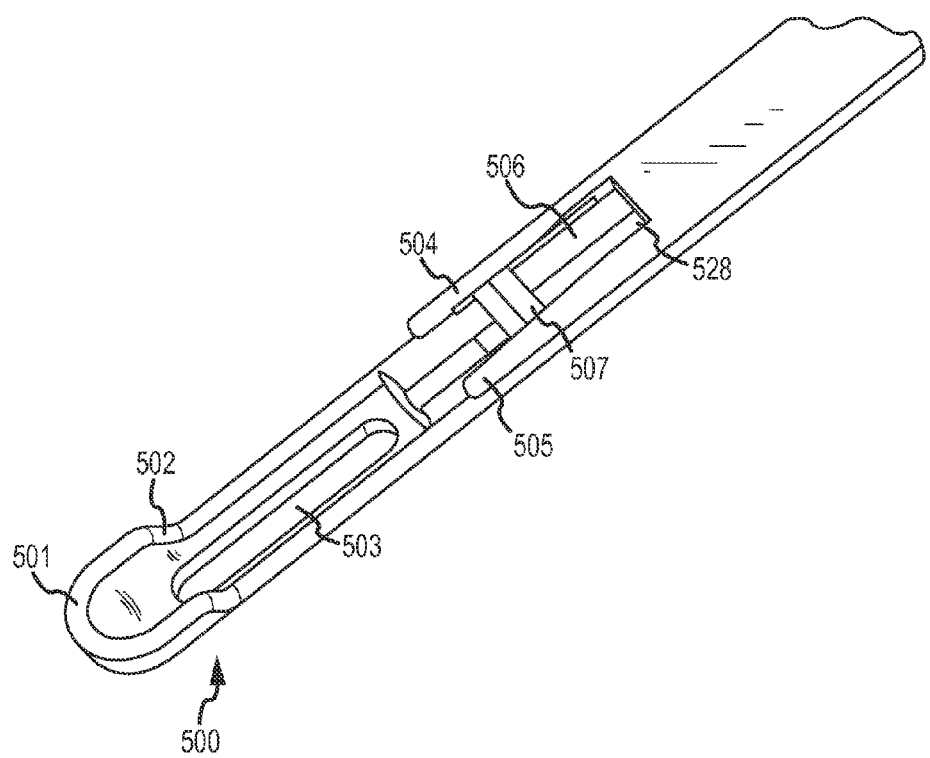
FIG. 35 is a perspective view of a probe according to certain embodiments.

Referring now to FIGS. 35-42, additional probe embodiments can be described. FIG. 35 shows a probe 500 adapted for use with the handpiece 420. This second embodiment of a probe can include a scoop retractor tongue 501 and a straight blade 507 in a retracted position. The side walls of the scoop retractor are tapered 502 and reach their greatest height at the distal end of the instrument. The base or floor of the retractor body has a hole or transparent window 503 therein so that the scope 506 has a full or nearly a full 360° spectrum of visualization including the zone beneath the instrument. The blade 507 is supported by two extensor arms 504, 505 that are side arms when the blade is retracted and become top and bottom arms when the blade is rotated for cutting. Another hole or transparent window 528 behind the blade 507 permits the scope 506 to see above the instrument when the blade 507 is retracted (at zero degrees or perpendicular to the longitudinal axis of the retractor body) even when the scope 506 is behind the blade.

Figure 36:
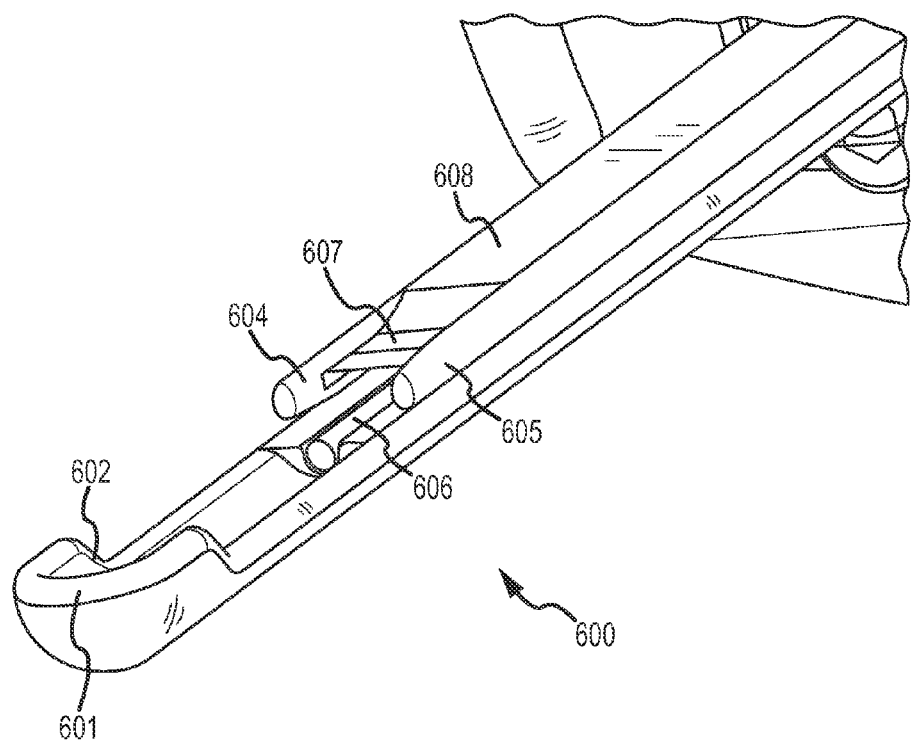
FIG. 36 is a perspective view of a probe according to certain embodiments.

FIG. 36 shows a probe 600 (from above and from the side) also adapted for use with the handpiece 420. This third embodiment of a probe 600 can be the same or similar to the second embodiment 500. However, the region behind the blade 607 can be an opaque solid 608 rather than a cutout hole or transparent solid. Due to this modification the blade 607 can be used to cut in one direction and visualization of the scope 606 through the top of the instrument is not provided when the scope 606 is positioned behind the blade 607 in the retractor shoot.

Figure 37:
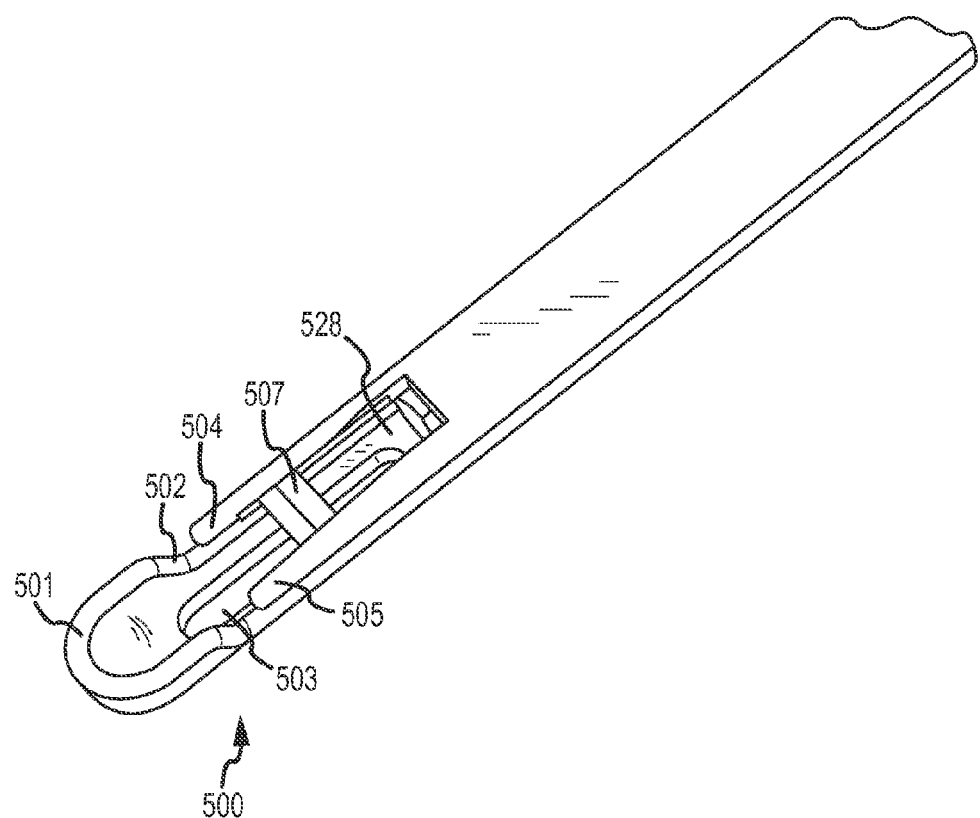
FIG. 37 is a perspective view of the probe of FIG. 35 with the blade in an advanced position.

FIG. 37 shows the disposable probe 500 (from above) according to the second embodiment, as in FIG. 35, with the blade 507 still in the inactive (non-cutting) retracted position (zero degrees) but having been advanced further down the retractor shoot so that it is closer to the distal end of the instrument.

Figure 38:
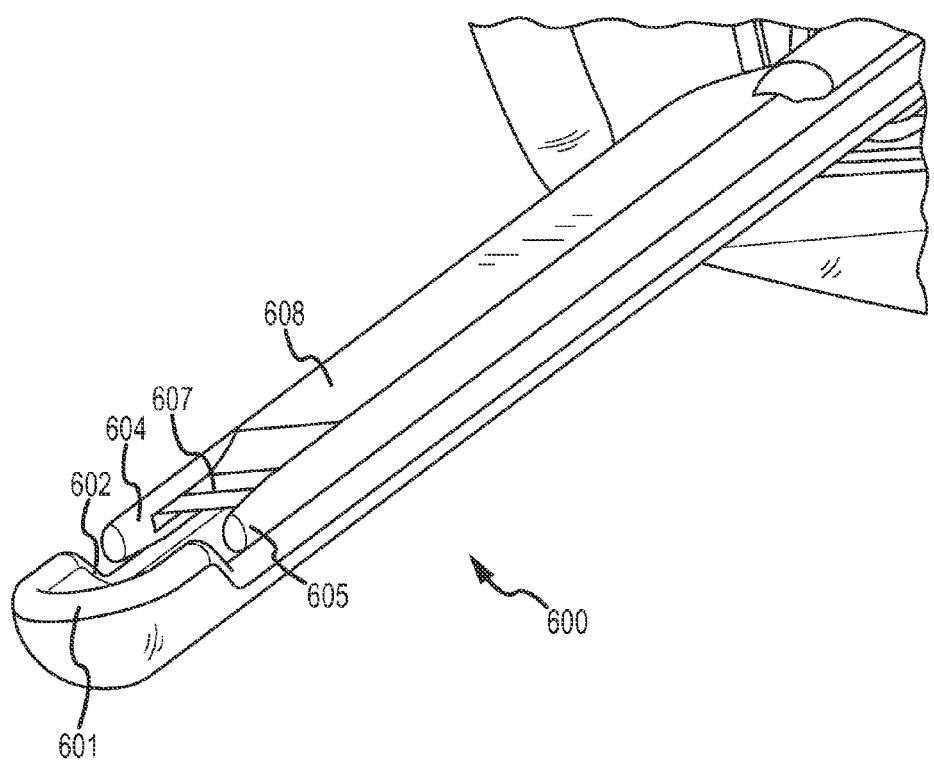
FIG. 38 is a perspective view of the probe of FIG. 36 with the blade in an advanced position.

FIG. 38 shows the disposable probe 600 (from above and from the side) according to the third embodiment, as in FIG. 36, with the blade 607 still in the inactive (non-cutting) retracted position (zero degrees) but having been advanced further down the retractor shoot so that it is closer to the distal end of the instrument.

Figure 39:
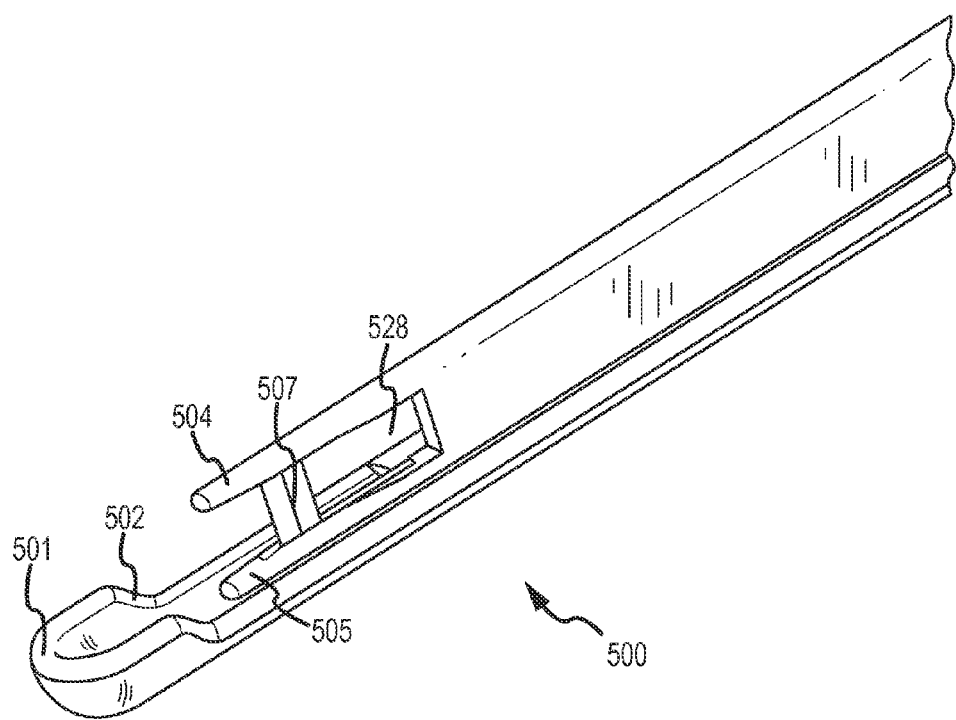
FIG. 39 is a perspective view of the probe of FIG. 35 with the blade in an advanced and deployed position.

FIG. 39 shows the disposable probe 500 (from the side) according to the second embodiment, as in FIGS. 35 and 38, with the blade 507 rotated 90 degrees to an active cutting position. The side extensor arms 504, 505, have become top and bottom support arms after rotation. Note that the region behind the blade 507 is open so that the tissue manipulation can be visualized well via the scope, as well as allowing cutting in a reverse (pulling) direction if the back edge of the blade 507 is sharp.

Figure 40:
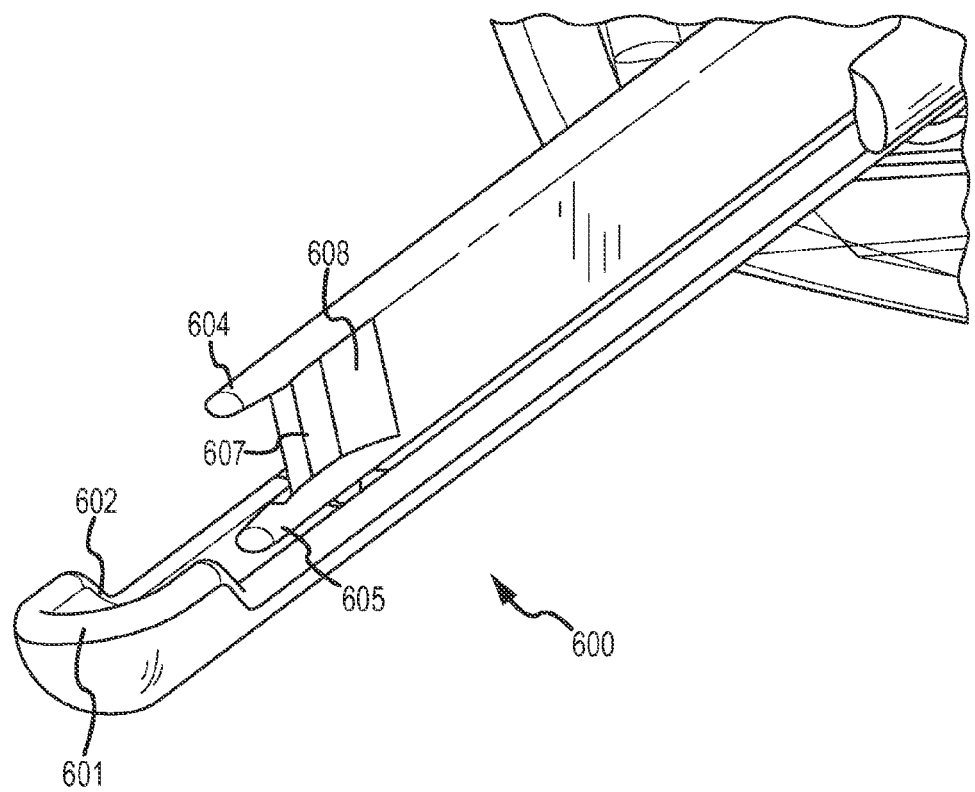
FIG. 40 is a perspective view of the probe of FIG. 36 with the blade in an advanced and deployed position.

FIG. 40 shows the disposable probe 600 (from the side) according to the third embodiment, as in FIGS. 36 and 38, with the blade 607 rotated 90 degrees to an active cutting position. The side extensor arms 604, 605 have become top and bottom support arms after rotation. Note that the region behind the blade is solid so that tissue does not become caught. However, cutting in a rearward direction is not provided.

Figure 41:
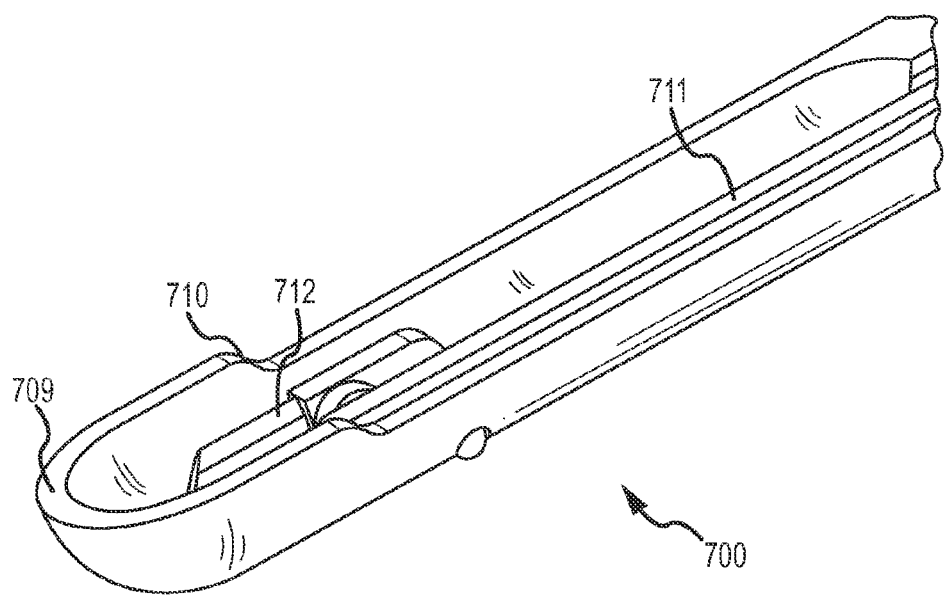
FIG. 41 is a perspective view of a probe according to certain embodiments.

FIG. 41 shows a disposable probe 700 (from above and from the side) adapted for use with either handpiece 100 or the handpiece 420. This fourth embodiment of a probe 700 can be similar to the first embodiment in that it includes a blade 712 and a single extensor arm 711. The arm can support the blade 712 both in an inactive retracted position inside a curved retractor scoop 709. The edges 710 of the retractor scoop 709 are substantially uniform in height and do not vary as much as in the second and third embodiments (compare to element 502/602 in FIG. 37 and FIG. 38).

Figure 42:
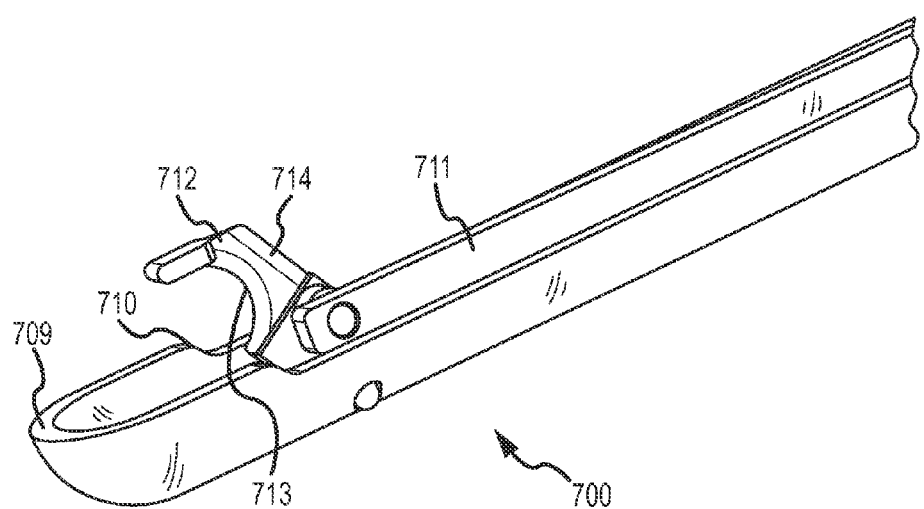
FIG. 42 is a perspective view of the probe of FIG. 41 with the blade in a deployed position.

FIG. 42 shows the disposable probe 700 (from the side) according to the fourth embodiment, as in FIG. 41, with the blade 712 raised up by the extensor arm 711 to an active cutting position. The blade 712 may have two sharp edges 713, 714 and no obstructions around either edge 713, 714 to facilitate bidirectional cutting. A first forward cutting edge 713 is curved and concave or hook-shaped. A second rear cutting edge 714 is straight and forward slanted. In contrast to the blade of the second and third 507/607 embodiments that is perpendicular to the longitudinal axis of the retractor body in its non-cutting position, the blade 712 of the fourth embodiment can be aligned parallel to the longitudinal axis of the retractor body even in its inactive position. While the blades 507/607 of the second and third embodiments are rotated about the longitudinal axis of the retractor body in order to cut, the blade 712 of the fourth embodiment, like the first 300, is raised up or rotated within the same plane of the longitudinal axis of the retractor body.

Figure 43:
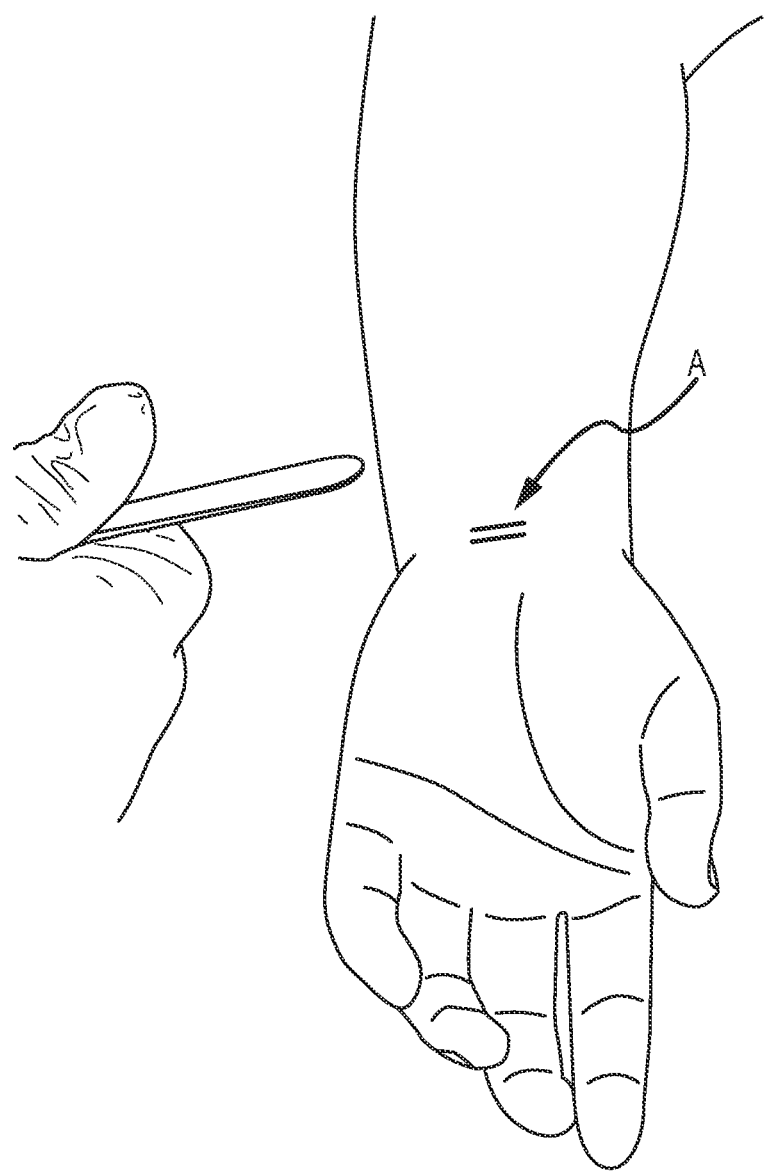
FIG. 43 is a view of a human wrist being prepared for a carpal tunnel release procedure.

FIG. 43 shows preparations for a carpal tunnel release (CTR) procedure on a wrist of a patient, the incision locations being indicated by the lines on the patient's wrist as indicated by arrow A.

Figure 44:
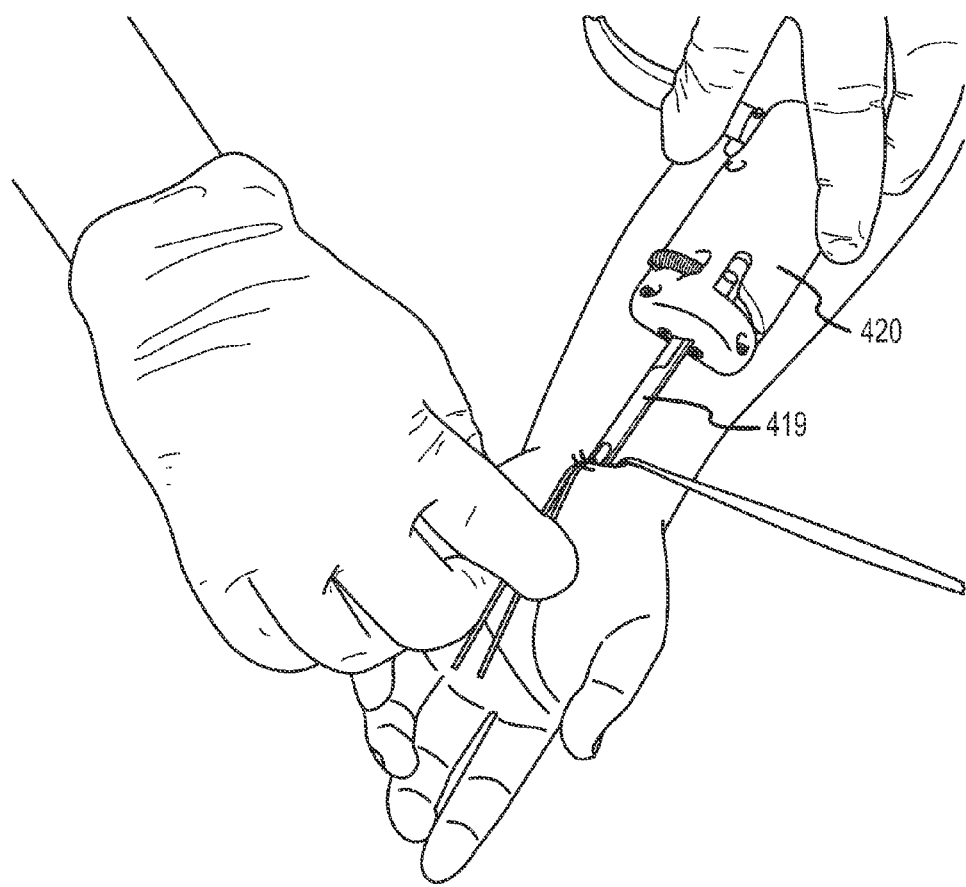
FIG. 44 is a view of the human wrist of FIG. 43 in the process of receiving a carpal tunnel release procedure.

FIG. 44 shows the distal end or tissue separator end of the probe 419, which extends distally from the handpiece 420 portion of the instrument, being inserted into the incision in the performance of a CTR procedure.

Figure 45:
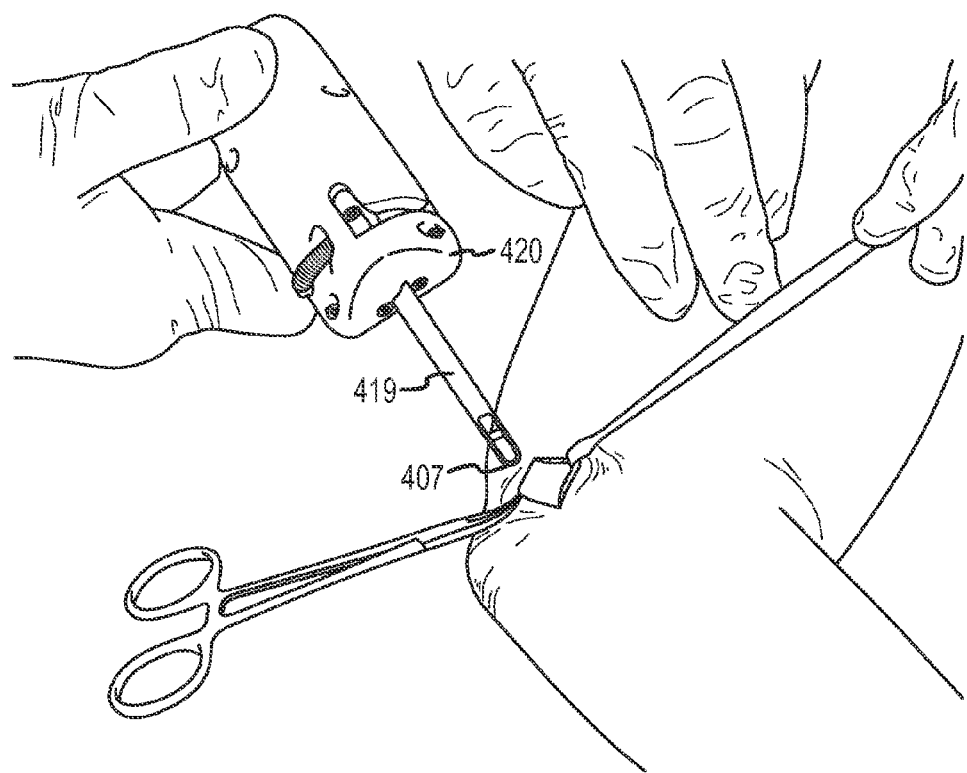
FIG. 45 is a view of a human elbow in the process of receiving a cubital tunnel release procedure.

FIG. 45 shows the distal end or tissue separator end of the probe 419, which extends distally from the handpiece 420 portion of the instrument, approaching an incision in the performance of a cubital tunnel release (CuTR) procedure.

Figure 46:
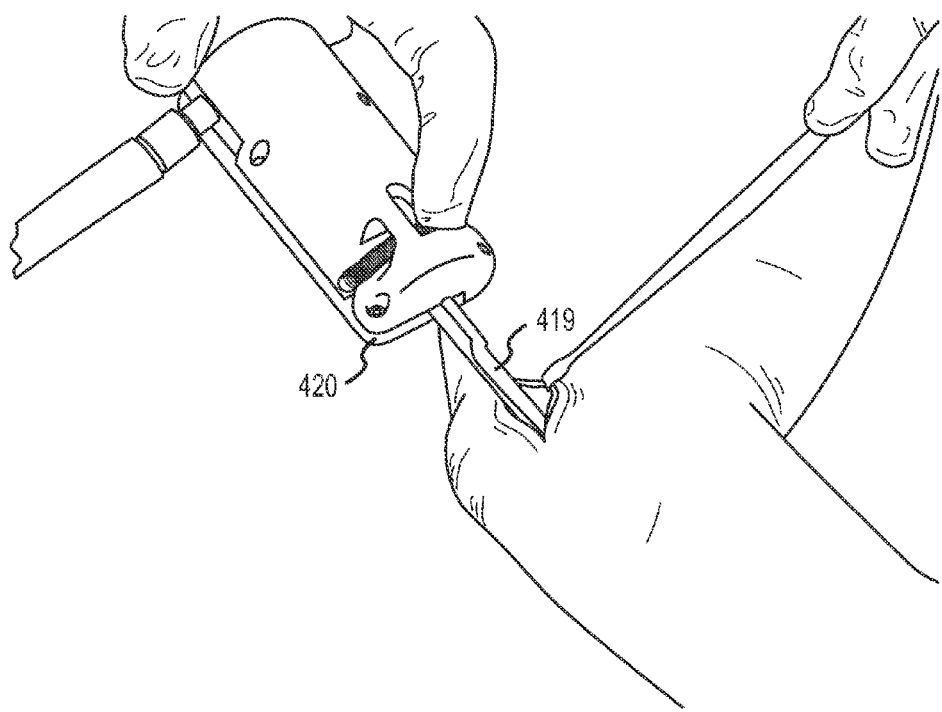
FIG. 46 is a view of the human elbow of FIG. 45 with a probe inserted into the elbow.

FIG. 46 shows the instrument of FIG. 41, wherein the distal end of the probe is in the incision during a CuTR procedure.

As described with respect to FIGS. 32-34, a knob on the handpiece can be used to change the blade between two different orientations by changing the position of the knob within an L-shaped cutout in the body of the handpiece. The knob can be locked in each position. The two positions may correspond to extension and retraction of the blade or they may be two different angular positions of an already extended blade, such as zero degrees and ninety degrees.

In one embodiment, the handpiece can be used to incrementally adjust or advance the angle of a blade on the probe and to lock the blade at each incremental position. The blade can be moved to and locked in position at every 15 degrees, every 20 degrees, every 30 degrees, or every 45 degrees from zero to 90 degrees or from zero to 180 degrees. Incremental locking features such as grooves or protrusions can be provided in association with a handpiece knob configured to engage them. In one embodiment, as in FIG. 34, a substantially Z-shaped cutout portion is provided in the body of the handle with several extra notches along the central branch of the Z. When a knob extending through the cutout region is in one arm of the Z, the blade is in a retracted position. When the knob is down the other arm of the Z, the blade is in a maximally extended position (i.e. 90 or 180 degrees). When the knob is down one of the intermediate side branches (extending off the central branch), the blade is extended but at an angle less than full extension (i.e. 15°, 30°, 45°, 60°, 75°, etc.).

Another feature of the handle is that it can have two gripping regions as shown in the embodiment of FIG. 33. A first gripping region can be provided for the palm of the hand with soft rubber for a comfortable no-slip grasp. For extra security against slippage superficial topography may be provided on the rubberized surface for greater friction. Superficial topography may be provided by any pattern having units with different heights from one another or from the base. With such a surface the surgeon is more likely to become aware of the instrument slipping or sliding due to tactile changes in the raised pattern pressing against the palm.

A second gripping region (or "grip head") can be provided for the thumb and the index finger. The grip head may be composed of a harder rubber and may optionally also have some superficial topography for greater traction between the surgeon's thumb and finger(s) and the instrument body. The second gripping region is closer to the patient's body when the instrument is in position. In one embodiment, the diameter of the second gripping region is smaller than that of the first palmar gripping region. A smaller diameter allows the surgeon's thumb and finger(s) to more easily encompass the distal portion of the handpiece so that it is easier to exercise greater dexterity and control. The perimeter of the second gripping region preferably has a chiseled or slanted surface so that it is not a perfect circle. If readjustment in the grip is needed it is easier to do so with edges to hold. The first or second gripping region may also be tapered with a smaller diameter at the distal end of the instrument compared to the proximal end.

The handpiece is not limited to attachment to cutting probes with blades and/or retractor probes. For example, other probes attachable to the handpiece may be used for diagnosis, delivery of drugs (or other therapeutic agents), delivery of clotting agents or sealants to induce hemostasis, etc. The function of the knob on the handpiece varies depending on the probe attached to it. For example, on drug delivery probes, the handpiece knob can be used to elute drugs and on diagnosis probes the knob can be used to deploy a needle to take a biopsy sample. The possibilities are unlimited and with the appropriate probe attached thereto the handpiece knob could also actuate lasers, microwavers, heating elements for cauterization, fluid supply for irrigation, etc.

According to the second embodiment, as shown in FIGS. 35, 38, and 39, a bidirectional blade is provided within a scooping retractor tongue. The distal end of the instrument body has U-shape horizontal cross-section. The distal end curves in a concave shape to form a mouth that pushes away tissue and catches particles of material cut above it. The base of the instrument provides a long shoot or pathway for unobstructed clarity during the cutting process. The base of the instrument has either an opening or a clear transparent window therein so that the scope can see through it as it is advanced over it. This feature is advantageous because when the instrument is positioned too high in enables a surgeon to recognize a target structure beneath through the hole or window in the instrument floor. The instrument can then be withdrawn slightly and inserted deeper so that the blade is appropriately positioned relative to a target structure (e.g., transverse carpal ligament or TCL).

To begin cutting, the blade is first advanced towards the distal end of the instrument (i.e. from position in FIG. 35 to position in FIG. 37). Next, the handpiece is manipulated to turn the blade and lock it in position at an angle desirable for cutting. FIG. 39 shows the blade in a 90° position for cutting. However, in a preferred embodiment, the blade stops, locks, and cuts at 45° for a smoother cut with a shearing effect. Cutting angles around 45° also appear to encourage better tissue regrowth during the healing process.

Regardless of the angle of the blade (in its inactive or cutting position), in one embodiment, the blade may be held between two extensor arms 504/505. This is in contrast to the blade of the first and fourth embodiment in which the blade is raised from one extensor arm. Additionally, irrespective of the lateral angle, the blade may point straight upward at a 90° angle between the distal end and the proximal end of the instrument. This is also in contrast to the blade 712 of the fourth embodiment in which the blade 712 may slant forward leaning towards the distal end of the instrument.

When the blade is in its cutting position, as in FIG. 39, the distal scoop end of the retractor can serve as a stop to catch the blade if it moves too far distally. The U-shaped scoop will act as a buttress against which the blade can be compressed for extra pressure when cutting especially fibrous or otherwise difficult tissue. As shown in FIG. 39, the retractor scoop can have tapered edges that are lower in height closer to the proximal end of the instrument body along the blade's path or runway. If the blade has two sharp edges the open region behind the blade permits it to cut in a backward direction (pulling) in addition to a forward direction (pushing).

The third embodiment, as shown in FIGS. 36, 38, and 40, is substantially similar to the second embodiment without the cutout regions. The region proximal to the blade on the instrument body is solid and opaque rather than open or transparent. This prevents visualization of a scope through the upper surface of the retractor body when the blade is at zero degrees in its inactive position and the retractor is behind the blade.

When the blade is turned, the solid upper surface or ceiling becomes the region behind the blade. Therefore, this change also prevents two-way cutting when the blade is between zero and 180 degrees in an active cutting position. If the region proximal to the blade is solid the blade can only cut by pushing and not by pulling.

An opaque solid floor or base on the retractor body prevents visualization through the bottom. Although the opaque solid rather than open or transparent structures in this embodiment may have disadvantages with respect to visualization and bidirectional cutting, they may also provide some advantages. With solid structures tissue cannot become inadvertently trapped in the retractor base, ceiling, or behind the blade and cannot be inadvertently cut. One way to avoid sacrificing the full 360° spectrum of visualization while still providing a solid structure to avoid accidentally catching tissue is to provide a transparent solid retractor base and ceiling. However, in some embodiments, opaque structures that shield the scope within the housing may be advantageous to avoid excessive light or blood on the endoscopic video monitor. To visualize a larger region when conditions are right the scope can always be extended outside of the housing past the blade and turned as necessary.

According to the fourth embodiment, as shown in FIGS. 41 and 42, a raised blade supported by a single extensor arm is used. As in the second embodiment, the blade has two sharp edges for bidirectional cutting. Bidirectional cutting may actually be easier when the blade is supported by only a single extensor arm, as in this fourth embodiment, because for backward cutting, when pulling the blade to the proximal end of the instrument body there is no upper arm (i.e. 504 in FIG. 39) to obstruct the entry space for tissue/ligaments/tendons, etc.

As illustrated in the fourth embodiment the shape of the blade can differ in the front and back. In the front a concave shaped hook blade is provided for cutting when pushing the blade in a forward direction. In the rear a forward slanted blade is provided for cutting when pulling the blade in a backward direction. In an alternative embodiment the front blade could have a convex shape and/or the rear blade could be slanted in the other direction, towards the proximal end of the instrument.

As shown in FIG. 42, when the blade of the third embodiment is in a retracted position it can be hidden completely within the elongated retractor scoop. Here the edges of the retractor scoop are substantially uniform in height rather than sharply tapered and the top of the body is completely open for maximum visualization above.

As can be understood from FIGS. 43 and 44, for a carpal tunnel release (CTR) procedure employing the device, similar to traditional open CTR surgery, endoscopic CTR surgery may be performed under either local, regional, or general anesthesia. With reference to FIG. 47, any and/or all of the steps or portions thereof can be included in a method of use of the devices described herein. A surgical site can be prepared. (Block 802) The procedure may be performed by placing an incision in the wrist (as indicated at arrow A in FIG. 43) or the palm or both of a patient. The incision may penetrate through the skin and any subcutaneous fat below the skin down to the antibrachial fascia. A small transverse incision may then be made through the antibrachial fascia to expose the bursa. Then the antibrachial fascia may be opened up longitudinally and distally. A synovial elevator may be used to elevate the synovium and locate the underside of the transverse carpal ligament. Once located, the synovium can continue to be elevated from the transverse carpal ligament (TCL).

A device for performing the procedure can be prepared. (Block 804). That is, the alignment features of a probe can be aligned with those of a handpiece and a retaining cap can be secured over the probe to attach it to the handpiece.

A first portion of the procedure can be performed. (Block 806) The distal end of the probe may then be inserted into the incision. An endoscope or other visualization device can be used to properly position the probe and adjustments can be made accordingly. A cannula may be provided on the probe upon first insertion for use in aiding the interchangeability of the probe and the cannula can be slid proximally to expose a probe tool. A first portion of a procedure can be performed with the first probe.

In one embodiment, a pressure detection probe may be provided with a cannula in place on the probe and the probe can be positioned within the carpal tunnel. The cannula can be slid proximally to expose the pressure detection probe and the pressure can be obtained. The cannula can then be slid distally to maintain the procedural position and the pressure detection probe can be removed.

The probe can then be exchanged with a second probed. (Block 808). The pressure detection probe can be removed from the handpiece by removing the retaining cap freeing the base assembly of the pressure detection probe from the handpiece. A new blade-type probe, for example probe 300, can be positioned against the distal end of the handpiece taking care to align the alignment features of the probe and the handpiece. The retaining cap can then be replaced to secure the blade-type probe in place.

A second portion of a procedure can then be performed (Block 810). The blade probe can then be reinserted into the procedure site and the scope can be used to visualize the target structures and other structures to ensure proper placement of the probe. In this embodiment, the device may be positioned so the open region of the probe distal region is facing upward toward the bottom side of the transverse carpal ligament. Having placed the device as described, the cannula can be withdrawn proximally along the length of the probe to expose the blade at a distal end of the probe and the blade may be used to sever the ligament. That is, the blade may be deployed or extended into its cutting position by releasing the locking mechanism and actuating the actuation mechanism to extend the blade. In one embodiment, this includes depressing the button to disengage the selector slide pin 130 from the rack 152 allowing the pivotal member 112 to be pivoted thereby advancing the linkage member 156 and causing the probe actuator 301 to move proximally and pivot the blade 342 into position. The handpiece and probe can then be moved distally and/or proximally to sever the ligament.

Additional probe exchanges can also be performed. (Block 812) For example, upon severing the ligament, the probe can again be interchanged with a pressure detecting probe to measure the tunnel pressure after severing the ligament.

It is noted that while a probe interchanging method has been described, the handpiece and probes shown and described herein can be used in single probe applications and the probes may be removed from the handpiece after the procedure is over and the probes can be discarded or sterilized. The devices and methods described are not limited to use in procedures requiring that multiple probes be interchanged. Additionally, the interchangeability is not limited to 2, 3, or any number of interchanges. The number of interchanges can be dictated by the procedure at hand and can depend on several factors including need for multiple tools, time, and other factors. Moreover, the method herein described is not limited to use of a pressure detection device and a blade-type probe. Other probe types can be used within the context of the method described and the steps of the method can remain.

It is noted that, in alternative to the above probe insertion and replacement, a pressure detection device could be inserted through a port of a blade-type device and the pressure in the tunnel may be measured prior to transecting the ligament. The pressure detection device may then also be used to measure the pressure in the tunnel after the transverse carpel ligament has been cut.

Additionally, as an alternative to placing the probe within the carpal tunnel, after an incision is made to access the flexor retinaculum, the instrument can be placed in the subcutaneous tissue under the skin of the palm, but superficial to the transverse carpal ligament (TCL) of the carpal canal. Using the scope, the TCL can be visualized and the cutting blade deployed in either "push" mode or "pull" mode to divide the TCL. The underlying median nerve can be visualized by the primary viewing port to ascertain that the nerve has been left intact with surrounding tissue (TCL) released.

Those skilled in the art will understand and appreciate the various approaches known in the art for performing a carpal tunnel release procedure. As such, use of the described embodiment as well as other embodiments of the instrument herein described will be apparent to those having skill in the art. Moreover, varying incision locations and procedures surrounding accessing and severing the ligament will also be apparent to those having skill in the art. These variances may be based on the surgeon's preference. The incision location may be in the flexion crease of the wrist as described above or may in the palm of the hand. The instrument may be inserted through a longitudinal (elongated) or transverse (wide) surface incision. The type of blade used and the direction of the sharp cutting edge may vary. Depending on the direction of the cutting edge, the location of its insertion (proximal or distal to the TCL), the TCL may be cut in a distal to proximal or proximal to distal direction. Depending on the thickness of the TCL and the thickness and sharpness of the blade, more or fewer passes of the blade may be required to completely release the TCL.

Similar steps can be included where alternative probes are used for similar or differing procedures. That is, where provided, a locking mechanism can be released and the actuation mechanism can be actuated to deploy a given probe tool. Movement of the handpiece can then be conducted to cause corresponding movement of the probe within the body to properly move and/or manipulate the probe tool, while visualization can be provided with a scope. Additional actuation of the probe tool can be provided (e.g., electrification, ultrasound, or other actuation) via a actuation button provided in communication with the probe tool. For example, in the case of a laser type probe tool, the probe may be inserted near or at a target location. The position of the probe tool relative to the prove can be adjusted via visualization with the scope and once properly placed, the laser can be electrified to electrically actuate the laser. Similar steps can occur for other probes requiring secondary or additional actuation.

As can be understood from FIGS. 45 and 46, a similar process to that described for CTR may be followed for a Cubital Tunnel Release (CuTR) procedure. For example, a brachial plexus nerve block may be used with lidocaine and buvipacaine and a tourniquet may be placed on the arm. The arm may be positioned in 90° abduction with the forearm supinated and the elbow flexed to 120°. The medial epicondyle may face anteriorly while the lateral epicondyle is supported by a stack of towels. Second, a 2-3 cm curvilinear longitudinal incision may be made between the medial epicondyle and the olecranon along the path of the ulnar nerve. The small incision size of the endoscopic procedure may be contrasted with the 6 cm (for simple decompression) to up to 15 cm (for transposition and medial epicondylectomy) incision sizes required in non-endoscopic surgical methods. Third, the incision may be deepened until the fascia of the flexor carpi ulnaris and Osborne's ligament (also called the cubital tunnel retinaculum) are exposed. Upon recognition, the flexor carpi ulnaris fascia and Osborne's ligament above the cubital tunnel may be cut to expose the ulnar nerve. Fourth, the retractor device may be inserted between the subcutaneous tissue and the superficial forearm fascia overlying the flexor carpi ulnaris. Fifth, an instrument as described herein may be introduced distally between the flexor carpi ulnaris muscle and the two heads of the flexor carpi ulnaris. Sixth, the instrument may be adjusted or manipulated to facilitate visualization and access to target structures. Seventh, the scope of the present instrument can be used to visualize the overlying fascia, the flexor carpi ulnaris muscle, and the ulnar nerve. Eighth, a probe tool in the form of a blade may be deployed as described above for releasing all possible sites of compression within the cubital tunnel under direct visualization projected to a monitor from the scope. The following sites may be divided with the blade to decompress the ulnar nerve: (i) the overlying fascia of the flexor carpi ulnaris muscle, (ii) Osborne's ligament (the cubital tunnel retinaculum) when present, (iii) the flexor pronator aponeurosis, (iv) the medial intermuscular septum, (v) the edge of the triceps, and (vi) the arcade of Struthers. Ninth, upon completion of the release of all potential sites of compression in the cubital tunnel in a range of up to 10 cm on each side of the medial epicondyle, the elbow may be brought through a full range of motion to determine whether there is any subluxation of the nerve. If subluxation is present a medial epicondylectomy may be performed through the same incision site during the same exposure. To conclude the endoscopic procedure, the tourniquet may be released, hemostatis obtained, and fine nylon sutures may be put in place as necessary. A soft elbow dressing may be applied and the patient may be encouraged to move the elbow on the first post-operative day. (See Tsai, et al. "Cubital Tunnel Release With Endoscopic Assistance: Results of a New Technique" *The Journal of Hand Surgery*, Vol. 24A No. 1 January 1999.)

The handpiece of the present invention is advantageous because it can be used with several different types of probes including disposable probes. Since the handpiece can be reuseable it is worth the investment to provide precision gripping and manipulation compared to cruder mechanisms used in handpieces in which the entire instrument (handpiece included) is disposed of after a procedure. The interchangeability of probes on the handpiece permits a surgeon to become comfortable with its actuation mechanism and to use one handpiece for several different procedures and on several different patients. Since the probes to be used with the handpiece come sterilized, hermetically sealed, and are disposable, cross-contamination is not an issue and cleaning time can be avoided. An angled periphery and variations in surface topography on the gripping region of the handle allow the surgeon to realize through tactile sensation if and when the instrument does slip and also allow the surgeon to more easily restore or adjust a grasp on the handle.

The handpiece can also be used with any standard scope and illumination systems for visualization. The body of the handpiece can open up and can include inlets so that standard endoscopic cameras can be fit inside and fiberoptic lighting cables threaded through its inner channels.

The disposable probes used for decompression the include a retractor portion that is atraumatic, curved, and compact. A stationary rather than mobile retractor zone can be more functional in constrained spaces of the body where decompression is needed. The stationary retractor can be pushed against tissue to clear a pathway for cutting by the blade as the whole instrument is advanced through tissue.

The blade on the probe may be able to move between a retracted safety position in which it is not exposed and one or more extended cutting position in which it is exposed. The blade can include two or more sharp edges for bidirectional cutting so that it can sever tissue by pushing or pulling. This enables a surgeon to more quickly resume cutting when one or more structure is missed on a first pass. By moving the blade back and forth the surgeon can effectively saw tough, fibrous tissue.

The body of the disposable probe can have one or more cutout portions through the floor/base and ceiling/top of the housing walls in order to provide unprecedented visualization above and below so that the retractor and blade can be more promptly positioned at a target site. Three hundred and sixty degree) (360°) visualization greatly reduces the risk of iatrogenic injury due to inadvertent cutting of blood vessels and nerves. Identifying anatomic structures through palpitation is not always an option and, when it is, visualization provides an assuring confirmation. In constrained spaces where decompression is used, major nerves and blood vessels (i.e. ulnar nerve, median nerve, etc.) are commonly in close proximity to target tissues, tendons, and ligaments. The visualization of these structures can assist a surgeon in avoiding damage to these structures.

Although the present invention has been described with reference to preferred embodiments, persons skilled in the art will recognize that changes may be made in form and detail without departing from the spirit and scope of the invention.

What is claimed is:

1. A probe for removable attachment to a handpiece, the probe comprising:
   a base assembly; and
   a procedure assembly extending from the base assembly, the procedure assembly comprising:
   an insertion member; and
   a probe tool positioned on the insertion member for selective deployment, the probe tool comprising a single blade having a top side opposite a bottom side, the bottom side having a concave cutting edge and the top side having a straight cutting edge with a blunt, non-cutting leading edge disposed between the top and bottom sides and extending distally from and transverse to the top and bottom side cutting edges, wherein a transverse body of the leading edge extends in a plane that defines an acute angle relative to a plane perpendicular to and inclusive of the straight cutting edge.

2. The probe of claim 1, wherein the insertion member includes a cavity at a distal end, the probe tool being positioned within the cavity.

3. The probe of claim 1, wherein the procedure assembly further comprises a window adapted for viewing of anatomical structures on a side of the insertion member opposite the probe tool.

4. The probe of claim 1 further comprising
   an actuation member extending along the insertion member of the procedure assembly, wherein
   the probe tool is attached to the actuation member via a hinge; and
   the non-cutting leading edge is disposed at a distal tip of the blade and is adapted to smoothly engage and separate target tissues from non-target tissues as the probe tool is caused to pivot about the hinge by the actuation member.

5. The probe of claim 4, wherein
   the non-cutting leading edge is formed in a duckbill shape; and
   when the leading edge is actuated in a first position, the leading edge clamps tissue against a base wall of the insertion member, and
   when the leading edge is actuated in a second position, the leading edge moves and holds non-target tissue out of the way of the blade.

6. The probe of claim 1, wherein
   the procedure assembly further comprises an actuation member pivotably connected to the blade that actuates the blade from a non-cutting position to a cutting position, and
   the procedure assembly is configured to move distally and proximally to cause the blade to cut target tissues with both the first cutting edge and the second cutting edge.

7. The probe of claim 1, wherein the insertion member further defines an aperture in a base wall of the insertion member positioned proximal to the probe tool.

8. The probe of claim 1, wherein the insertion member further comprises a first groove for receiving an auxiliary device and a second groove for receiving a probe actuator operably connected to the probe tool.

9. The probe of claim 8, wherein
   the insertion member further defines an aperture in a base wall of the insertion member and the aperture is positioned proximal to the probe tool;
   the first groove receiving the auxiliary device and the probe tool are centered along a longitudinal axis of the insertion member; and
   the second groove is positioned parallel and laterally adjacent to the first groove and the aperture in the base wall of the insertion member.

10. The probe of claim 8, wherein the auxiliary device is selected from the group consisting of a scope, a light source, an air source, a fluid source, or an electrical source.

11. The probe of claim 8, wherein the auxiliary device includes one or more fiber optic cores.

12. A method of performing a release procedure comprising
   inserting at least a portion of a probe into an incision site, the probe comprising a base assembly and a procedure assembly, the procedure assembly comprising an insertion member and a probe tool in a non-deployed state, the insertion member comprising a first groove for receiving an auxiliary device and a second groove for receiving a probe actuator operably connected to the probe tool and the probe tool comprising a single blade having a top side opposite a bottom side, the bottom side having a concave cutting edge and the top side having a straight cutting edge with a blunt, non-cutting, leading edge disposed between the top and bottom sides and extending distally from and transverse to the top and bottom side cutting edges, wherein a transverse body of the leading edge extends in a plane that defines an acute angle relative to a plane perpendicular to and inclusive of the straight cutting edge;

positioning the probe at a target structure;
deploying the probe tool from the procedure assembly; and
performing a release procedure with the probe tool.

13. The method of claim 12, wherein the release procedure is a carpal tunnel release procedure, the incision site is at the wrist, and the target structure includes a transverse carpal ligament.

14. The method of claim 12, wherein the release procedure is a cubital tunnel release procedure, the incision site is at the elbow and the target structure includes at least one of a flexor carpi ulnaris fascia, Osborne's ligament, a flexor pronator aponeurosis, the medial intermuscular septum, an edge of the triceps, or the arcade of Struthers.

15. The method of claim 12, wherein the positioning operation comprises visualizing non-target structures via an aperture in a base wall of the insertion member.

16. The method of claim 12, wherein the performing operation further comprises moving the probe tool proximal and distal of the target tissue to cut the target tissue, thereby releasing the target tissue.

17. The method of claim 12, wherein the auxiliary device includes one or more fiber optic cores.

18. A probe for removable attachment to a handpiece, the probe comprising
a base assembly; and
a procedure assembly extending from the base assembly, the procedure assembly comprising:
an insertion member having a distal end with a base wall, sidewalls, and an open top such that a cavity is defined therein, wherein the base wall of the distal end defines a bottom portion of the cavity, and a window opposite the open top adapted for viewing of anatomical structures is defined within the cavity, the window being open and exposed to the anatomical structures below the base wall; and
a probe tool positioned within the cavity opposite the window and adapted for selective deployment.

19. The probe of claim 18, wherein the probe tool comprises a blade with an arcuate first cutting edge and a straight second cutting edge opposite the first cutting edge.

20. The probe of claim 19, wherein the blade further comprises a blunt, non-cutting leading edge disposed between the first and second edges.

21. The probe of claim 18, wherein the insertion member further comprises a first groove for receiving an auxiliary device and a second groove for receiving a probe actuator operably connected to the probe tool.

22. The probe of claim 18, wherein the open top and the window of the insertion member provide approximately 360 degrees of visualization of target and non-target anatomical structures.

* * * * *